United States Patent
Chang et al.

(10) Patent No.: US 10,040,848 B2
(45) Date of Patent: *Aug. 7, 2018

(54) CHIMERIC AND HUMANIZED ANTI-HISTONE ANTIBODIES

(71) Applicant: Immunomedics, Inc., Morris Plains, NJ (US)

(72) Inventors: Chien-Hsing Chang, Downingtown, PA (US); Hans J. Hansen, Diamondhead, MS (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/887,488

(22) Filed: Feb. 2, 2018

(65) Prior Publication Data
US 2018/0171003 A1    Jun. 21, 2018

Related U.S. Application Data

(62) Division of application No. 15/713,031, filed on Sep. 22, 2017, now Pat. No. 9,920,116, which is a division of application No. 15/487,747, filed on Apr. 14, 2017, now Pat. No. 9,809,646, which is a division of application No. 15/005,596, filed on Jan. 25, 2016, now Pat. No. 9,657,093, which is a division of application No. 14/620,315, filed on Feb. 12, 2015, now Pat. No. 9,278,129, which is a division of application No. 14/180,646, filed on Feb. 14, 2014, now Pat. No. 8,987,421.

(60) Provisional application No. 61/765,150, filed on Feb. 15, 2013.

(51) Int. Cl.
| | |
|---|---|
| C07K 16/18 | (2006.01) |
| A61K 39/395 | (2006.01) |
| C07K 16/24 | (2006.01) |
| C07K 16/28 | (2006.01) |
| A61K 31/573 | (2006.01) |
| A61K 39/00 | (2006.01) |

(52) U.S. Cl.
CPC ............ *C07K 16/18* (2013.01); *A61K 31/573* (2013.01); *A61K 39/3955* (2013.01); *C07K 16/24* (2013.01); *C07K 16/248* (2013.01); *C07K 16/2833* (2013.01); *C07K 16/2851* (2013.01); *C07K 16/2887* (2013.01); *A61K 2039/507* (2013.01); *C07K 2317/24* (2013.01); *C07K 2317/31* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,645,493 B1 | 11/2003 | Bucala et al. | |
| 7,312,318 B2 | 12/2007 | Hansen et al. | |
| 8,088,357 B2 | 1/2012 | Goletz et al. | |
| 8,119,101 B2 | 2/2012 | Byrd et al. | |
| 8,716,218 B2 | 5/2014 | Esmon et al. | |
| 8,987,421 B2 * | 3/2015 | Chang ................... | C07K 16/18 424/130.1 |
| 2003/0013122 A1 | 1/2003 | Bucala et al. | |
| 2006/0286611 A1 | 12/2006 | Zempleni et al. | |
| 2007/0003543 A1 | 1/2007 | Datta et al. | |
| 2012/0231016 A1 | 9/2012 | Tseng et al. | |

FOREIGN PATENT DOCUMENTS

| | | |
|---|---|---|
| WO | 2009061918 A1 | 5/2009 |
| WO | 2012155039 A1 | 11/2012 |

OTHER PUBLICATIONS

Abrams et al., "Circulating histones are mediators of trauma-associated lung injury", Am J Respir Crit Care Med. Jan. 15, 2013;187(2)160-9.
Ammollo et aL, "Extracellular histones increase plasma thrombin generation by impairing thrombomodulin-dependent protein C activation", J Thromb Haemost. Sep. 2011;9(9):1795-803.
Esmon, CT., "Extracellular histones zap platelets", Blood. Sep. 29, 2011;118(13):3456-7.
Esmon et al., "Innate immunity and coagulation", J Thromb Haemost. Jul. 2011;9 Suppl 1:182-8.
Huang et al., Endogenous histones function as alarmins in sterile inflammatory liver injury through Toll-like receptor 9 in mice, Hepatology. Sep. 2, 2011;54(3):999-1008.
Semeraro et al., "Extracellular histones promote thrombin generation through platelet-dependent mechanisms: involvement of platelet TLR2 and TLR4", Blood. Aug. 18, 2011;118(7):1952-61.
Xu et al., "Extracellular histones are mediators of death through TLR2 and TLR4 in mouse fatal liver injury", J Immunol. Sep. 1, 2011;187(5):2626-31.

(Continued)

*Primary Examiner* — Sharon X Wen
(74) *Attorney, Agent, or Firm* — Richard A. Nakashima

(57) ABSTRACT

The present invention concerns chimeric or humanized antibodies or antigen-binding fragments thereof that comprise specific CDR sequences, disclosed herein. Preferably, the antibodies or fragments comprise specific heavy and light chain variable region sequences disclosed herein. More preferably, the antibodies or fragments also comprise specific constant region sequences, such as those associated with the nG1m1,2 or Km3 allotypes. The antibodies or fragments may bind to a human histone protein, such as H2B, H3 or H4. The antibodies or fragments are of use to treat a variety of diseases that may be associated with histones, such as autoimmune disease (e.g., SLE), atherosclerosis, arthritis, rheumatoid arthritis, edema, sepsis, septic shock, hyperinflammatory disorder, infectious disease, inflammatory disease, immune dysregulatory disorder, GVHD, transplant rejection, atherosclerosis, asthma, a coagulopathy, myocardial ischemia, thrombosis, nephritis, inflammatory liver injury, acute pancreatitis, ischemia-reperfusion injury, stroke, cardiovascular disease, and burn.

28 Claims, 7 Drawing Sheets

(56) References Cited

OTHER PUBLICATIONS

Xu et al., "Extracellular histones are major mediators of death in sepsis", Nat Med. Nov. 2009;15(11):1318-21.
Xu et al., "Inflammation, innate immunity and blood coagulation", Hamostaseologie. Jan. 2010;30(1):5-6, 8-9.
Allam et al., "Histones from Dying Renal Cells Aggravate Kidney Injury via TLR2 and TLR4", J Am Soc Nephrol. Aug. 2012;23(8):1375-88.
Astiz et al., "Septic shock", Lancet. May 16, 1998;351(9114)1501-5.
Berends et al., "Nuclease expression by *Staphylococcus aureus* facilitates escape from neutrophil extracellular traps", J Innate Immun. 2010;2(6):576-86.
Bernard et al., "Efficacy and safety of recombinant human activated protein C for severe sepsis", N Engl J Med. Mar. 8, 2001;344(10):699-709.
Burger-Kentischer et al., "Expression of macrophage migration inhibitory factor in different stages of human atherosclerosis", Circulation. Apr. 2, 2002;105(13):1561-6.
Calandra et al., "Protection from septic shock by neutralization of macrophage migration inhibitory factor", Nat Med. Feb. 2000;6(2):164-70.
Caudrillier et al., "Platelets induce neutrophil extracellular traps in transfusion-related acute lung injury", J Clin Invest. Jul. 2, 2012;122(7):2661-71.
Chow et al., "Statins enhance formation of phagocyte extracellular traps", Cell Host Microbe. Nov. 18, 2010;8(5):445-54.
Creemers et al., "Epitope recognition in histone H1 by SLE autoantibodies in the presence of a DNA-ligand", Autoimmunity. 1992;12(3):167-74.
De Meyer et al., "Extracellular chromatin is an important mediator of ischemic stroke in mice", Arterioscler Thromb Vasc Biol. Aug. 2012;32(8):1884-91.
Dieker et al., "Mimotopes for lupus-derived anti-DNA and nucleosome-specific autoantibodies selected from random peptide phage display libraries: facts and follies", J Immunol Methods. Jan. 2005;296(1-2):83-93.
Fleming et al., "Accelerated ischemia/reperfusion-induced injury in autoimmunity-prone mice", J Immunol. Sep. 15, 2004;173(6):4230-5.
Fleming et al., "Anti-phospholipid antibodies restore mesenteric ischemia/reperfusion-induced injury in complement receptor 2/complement receptor 1-deficient mice", J Immunol. Dec. 1, 2004;173(11):7055-61.
Frese-Schaper et al., "Reversal of established lupus nephritis and prolonged survival of New Zealand black x New Zealand white mice treated with the topoisomerase I inhibitor irinotecan", J Immunol. Feb. 15, 2010;184(4):2175-82.
Friggeri et al., "Extracellular histones inhibit efferocytosis", Mol Med. Jul. 18, 2012;18:825-33.
Fuchs et al., "Extracellular DNA traps promote thrombosis", Proc Natl Acad Sci U S A. Sep. 7, 2010;107(36):15880-5.
Gillrie et al., "Plasmodium falciparum histones induce endothelial proinflammatory response and barrier dysfunction", Am J Pathol. Mar. 2012;180(3):1028-39.
Jiang et al., "The expression of plasma nucleosomes in mice undergoing in vivo apoptosis", Clin Immunol. Feb. 2003;106(2):139-47.
Kimura et al., "Kinetics of core histones in living human cells: little exchange of H3 and H4 and some rapid exchange of H2B", J Cell Biol. Jun. 25, 2001;153(7):1341-53.
Kramers et al., "Specificity of monoclonal anti-nucleosome autoantibodies derived from lupus mice", J Autoimmun. Dec. 1996;9(6):723-9.
Larosa et al., "Immune aspects of sepsis and hope for new therapeutics", Curr Infect Dis Rep. Oct. 2012;14(5):474-83.
Lee et al., "Histone H4 is a major component of the antimicrobial action of human sebocytes", J Invest Dermatol. Oct. 2009;129(10):2489-96.
Leung et al., "Construction and characterization of a humanized, internalizing, B-cell (CD22)-specific, leukemia/lymphoma antibody, LL2", Mol Immunol. Dec. 1995;32(17-18):1413-27.
Monestier et al., "Shared idiotypes and restricted immunoglobulin variable region heavy chain genes characterize murine autoantibodies of various specificities", J Clin Invest. Sep. 1986;78(3):753-9.
Monestier et al., "Monoclonal anti-histone H1 autoantibodies from MRL Ipr/lpr mice", Mol Immunol. Aug. 1989;26(8):749-58.
Monestier et al., "Antihistone antibodies in antinuclear antibody-positive juvenile arthritis", Arthritis Rheum. Dec. 1990;33(12):1836-41.
Monestier, M., "Variable region genes of anti-histone autoantibodies from a MRL/Mp-lpr/lpr mouse", Eur J Immunol. Jul. 1991;21(7):1725-31.
Monestier et al., "Antibodies to histones in systemic lupus erythematosus and drug-induced lupus syndromes", Rheum Dis Clin North Am. May 1992;18(2):415-36.
Monestier et al., "Structure and binding properties of monoclonal antibodies to core histones from autoimmune mice", Mol Immunol. Aug. 1993;30(12):1069-75.
Monestier et al., "Induction of anti-polycation antibodies in H-2s mice by immunization with nuclear antigens", Mol Immunol. Jan. 1997;34(1):39-51.
Monestier et al., "Molecular and structural properties of three autoimmune IgG monoclonal antibodies to histone H2B", J Biol Chem. May 5, 2000;275(18):13558-63.
Mostoslavsky et al., "Lupus anti-DNA autoantibodies cross-react with a glomerular structural protein: a case for tissue injury by molecular mimicry", Eur J Immunol. Apr. 2001;31(4):1221-7.
Neeli et al., "Divergent members of a single autoreactive B cell clone retain specificity for apoptotic blebs", Mol Immunol. Mar. 2007;44(8):1914-21.
Olins et al., "The human granulocyte nucleus: Unusual nuclear envelope and heterochromatin composition", Eur J Cell Biol. May 2008;87(5):279-90.
Olins et al., "An epichromatin epitope: persistence in the cell cycle and conservation in evolution", Nucleus. Jan.-Feb. 2011;2(1):47-60.
Prudovsky et al., "Phosphatidylserine colocalizes with epichromatin in interphase nuclei and mitotic chromosomes", Nucleus. Mar. 1, 2012;3(2):200-10.
Radic et al., "Nucleosomes are exposed at the cell surface in apoptosis", J Immunol. Jun. 1, 2004;172(11):6692-700.
Riedemann et al., "The enigma of sepsis", J Clin Invest. Aug. 2003;112(4):460-7.
Rifkin et al., "Immune complexes present in the sera of autoimmune mice activate rheumatoid factor B cells", J Immunol. Aug. 1, 2000;165(3):1626-33.
Salgame et al., "An ELISA for detection of apoptosis", Nucleic Acids Res. Feb. 1, 1997;25(3):680-1.
The Merck Manuals Professional Edition, [online]. Kenilworth, NJ: Merck Sharp & Dohme Corp, 2015. [retrieved on Jul. 13, 2015]. Retrieved from the Internet: < http://www.merckmanuals.com/professional/genitourinary-disorders/glomerular-disorders/rapidly-progressive-glomerulonephritis-rpgn>. Rapidly Progressive Glomerulonephritis (RPGN). See pp. 1-6.
The Merck Manuals Online Medical Library, [online]. Whitehouse Station, NJ: Merck Research Laboratories, 2006-2007. [retrieved on Nov. 19, 2007]. Retrieved from the Internet: < URL: http://www.merck.com/mmpe/print/sec06/ch068/ch068a.html>. Sepsis and Septic Shock. See pp. 1-5.
Redl et al., "Animal models as the basis of pharmacologic intervention in trauma and sepsis patients", World J Surg. May 1996;20(4):487-92.
Standen et al., "Septic Shock", N Engl J Med 2000, 343:447-448.
Toussaint et al., "Immunoglobulins in adult sepsis and septic shock", Curr Infect Dis Rep. Oct. 2012;14(5):522-9.
Ullal et al., "Microparticles as antigenic targets of antibodies to DNA and nucleosomes in systemic lupus erythematosus", J Autoimmun. May 2011;36(3-4):173-80.
Van Amersfoort et al., "Receptors, mediators, and mechanisms involved in bacterial sepsis and septic shock", Clin Microbiol Rev. Jul. 2003;16(3):379-414.

(56) References Cited

OTHER PUBLICATIONS

Van Bavel et al., "Apoptosis-associated acetylation on histone H2B is an epitope for lupus autoantibodies", Mol Immunol. Dec. 2009;47(2-3):511-6.
Van Bruggen et al., "Nucleosomes and histones are present in glomerular deposits in human lupus nephritis", Nephrol Dial Transplant. Jan. 1997;12(1):57-66.
Yasuda et al., "Requirement for DNA CpG content in TLR9-dependent dendritic cell activation induced by DNA-containing immune complexes", J Immunol. Sep. 1, 2009;183(5):3109-17.

* cited by examiner

Sequence:

QVQLQQSGAELVRPGASVKLSCTASGFNIK*DDYLH*WVKQRPEQGLE
                                                              CDRH-1
WIG*WIDPENGDTEYASKFQG*KATITADTSSNTAYLQLSSLTSEDTAVY
    CDRH-2
YCSS*PLVHLRTFAY*WGQGTLVTVS
     CDRH-3

Published Sequence:

<u>E</u>IQLQQSGAELV<u>XX</u>GASVKLSCTASGFNIK*DDYLH*WVKQRPEQGLE
                                                              CDRH-1
WIG*WIDPENGDTEYASKFQG*KATITADTSSNTAYLQLSSLTSEDTAVY
    CDRH-2
YCSS*PLVHLRTFAY*WGQGTLVTVS
     CDRH-3

VK

Sequence:

DIQLTQSPASLAVSLGQRATISC*RASESVDSYDNSLH*WFQQKPGQ
                                      CDRL-1
PPKLLIY*LASNLES*GVPARFSGSGSRTDFTLTIDPVEADDAATYYC
      CDRL-2
*QQNNEDPWT*FGGGTKLEIKR
   CDRL-3

Published Sequence:

NI<u>V</u>LTQSPASLAVSLGQRATISC*RASESVDSYDNSLH*WFQQKPGQ
                                      CDRL-1
PPKLLIY*LASNLES*GVPARFSGSGSRTDFTLTIDPVEADDAATYYC
      CDRL-2
*QQNN*
   CDRL-3

Sequence:

QVQLQESGAELVKPGASVKLSCKASGYTFT*SYWMHW*VKQRPGQ
                 CDRH-1
GLEWIG*NIDPSDSETHYNQKFKD*KATLTVDKSSNTAYMQLSSLTS
   CDRH-2
EDSAVFYCAR*EKITDDYNYFDY*WGQGTTLTVS
     CDRH-3

Published Sequence:

QVQLQQPGAELVKPGASVKLSCKASGYTFT*SYWMHW*VKQRPGQ
                 CDRH-1
GLEWIG*NIDPSDSETHYNQKFKD*KATLTVDKSSNTAYMQLSSLTS
   CDRH-2
EDSAVFYCAR*EKITDDYNYFDY*WGQGTTLTVS
     CDRH-3

VK

Sequence:

DIQLTQSPASLALSLRQRATISC*RASESVDSYGNSFMH*WYQQ
             CDRL-1
KPGQPPKLLIY*HASNLES*GVPARFSGSGSRTDFTLTIDPVEAD
    CDRL-2
DAATYYC*QQNNEDPLT*FGAGTKLELKR
    CDRL-3

Published Sequence:

KI*VL*TQSPASLALSLRQRATISC*RASESVDSYGNSFMH*WYQQ
             CDRL-1
KPGQPPKLLIY*HASNLES*GVPARFSGSGSRTDFTLTIDPVEAD
    CDRL-2

DAATYY

Sequence:
```
                        CDRH-1
QVKLQQSGPELVKPGASVKMSCRASGYTFTSYVMYWVKQKPG
              CDRH-2
QGLEWIGYINPYNDGTKYNEKFKGKATLTSDKSSSTAYMELSSL
       CDRH-3
TSEDSAVYYCAGPGDGYPFDYWGQGTTLTVS
```

Published Sequence:
```
                         CDRH-1
EVQLQQSGPELVRPGASVKMSCRASGYTFTSYVMYWVKQKPG
              CDRH-2
QGLEWIGYINPYNDGTKYNEKFKGKATLTSDKSSSTAYMELSSL
       CDRH-3
TSEDSAVYYCAGPGDGYPFDYWGQGTTLTVS
```

VK

Sequence:
```
                              CDRL-1
DVLMTQTPLSLPVSLGDQASISCRSSQSIVHSNGNTYLEWYLQK
                    CDRL-2
PGQSPKLLIYKVSNRFSGVPDRFSGSGSGTDFTLKISRVEAED
       CDRL-3
LGVYYCFQGSHVPYTFGSGTKLEIKR
```

Published Sequence:
```
                              CDRL-1
DVLMTQTPLSLPVSLGDQASISCRSSQSIVHSNGNTYLEWYLXK
                    CDRL-2
PGQSPKLLIYKVSNRFSXVPDRFSGSGSGXGTDFTLKISRVEAED

LGVY
```

FIG. 4 hIMMU-H4 VH

CDRH-1
QVQLQQSGAEVKKPGSSVKVSCKASGYTFT*DDYLH*WVKQAPGQGLE
CDRH-2
WIG*WIDPENGDTEYASKFQ*GKATLTADESTNTAYMELSSLRSEDTAFY
CDRH-3
YCSS*PLVHLRTFAY*WGQGTTVTVSS hIMMU-H4 VK

CDRL-1
DIQLTQSPSSLSASVGDRVTMTC*RASESVDSYDNSLH*WFQQKPGK
CDRL-2
APKPWIY*LASNLES*GVPVRFSGSGSGTDYTFTISSLQPEDIATYYC
CDRL-3
QQ*NNEDPW*TFGGGTKLEIKR

*FIG. 5* hIMMU-H3 VH

CDRH-1
QVQLQQSGAEVKKPGSSVKVSCKASGYTFTSYWMHWVKQAPGQ
             CDRH-2
GLEWIGNIDPSDSETHYNQKFKDKATLTADESTNTAYMELSSLRS
   CDRH-3
EDTAFYYCAREKITDDYNYFDYWGQGTTVTVSS hIMMU-H3 VK

CDRL-1
DIQLTQSPSSLSASVGDRVTMTCRASESVDSYGNSFMHWFQQ
             CDRL-2
KPGKAPKPWIYHASNLESGVPVRFSGSGSGTDYTFTISSLQPE
   CDRL-3
DIATYYCQQNNEDPLTFGGGTKLEIKR

FIG. 6 hIMMU-H2B VH

CDRH-1
QVQLQQSGAEVKKPGSSVKVSCKASGYTFT*SYVMY*WVKQAPG
　　　　　　　　　　　　　　　CDRH-2
QGLEWIG*YINPYNDGTKYNEKFKG*KATLTADESTNTAYMELSSL
　　　　CDRH-3
RSEDTAFYYCAR*PGDGYPFDY*WGQGTTVTVSS hIMMU-H2B VK

CDRL-1
DIQLTQSPSSLSASVGDRVTMTCR*SSQSIVHSNGNTYLE*WFQQK
　　　　　　　CDRL-2
PGKAPKPWIYK*VSNRFS*GVPVRFSGSGSGTDYTFTISSLQPED
　　　　　CDRL-3
IATYYC*FQGSHVPYT*FGGGTKLEIKR

SEQUENCE LISTING

<160> NUMBER OF SEQ ID NOS: 128

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

```
<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 8
<211> LENGTH: 51
<212> TYPE: PRT
<213> ORGANISM: Homo sapiens

<400> SEQUENCE: 8

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30
```

```
Arg Pro Met Ala Phe Leu Arg Glu Tyr Phe Glu Lys Leu Glu Lys Glu
            35                  40                  45

Glu Ala Lys
    50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
            35                  40                  45

Asn Arg Gln Ile Leu Ala
    50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
            35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
            35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
            35                  40
```

```
<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40
```

```
<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40
```

```
<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40
```

```
<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40
```

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 32

Asn Ile Glu Tyr Leu Ala Lys Gln Ile Val Asp Asn Ala Ile Gln Gln
1               5                   10                  15

Ala

```
<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
1               5                   10                  15

Ala
```

```
<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ile Glu Tyr Leu Ala Lys Asn Ile Val Asp Asn Ala Ile Gln Gln
1               5                   10                  15

Ala
```

```
<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Leu Ala Lys Gln Ile Val Asp Asn Ala Ile Gln Gln
1               5                   10                  15

Leu
```

```
<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr His Ala Lys Gln Ile Val Asp His Ala Ile His Gln
1               5                   10                  15

Ala
```

```
<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Tyr Gln Phe Ala Asp Arg Phe Ser Glu Leu Val Ile Ser Glu
1               5                   10                  15

Ala Leu
```

```
<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr
```

```
<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
            20

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala
```

```
<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25
```

```
<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

```
Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
```

-continued

```
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val
```

```
<400> SEQUENCE: 87

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
                20                  25                  30

Val Xaa Tyr Phe Xaa Xaa Leu Xaa Xaa Xaa Xaa
            35                  40

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 88

Xaa Xaa Xaa Xaa Xaa Ala Xaa Xaa Ile Val Xaa Xaa Ala Ile Xaa Xaa
1               5                   10                  15

Xaa

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Asp Tyr Leu His
1               5

<210> SEQ ID NO 91
<211> LENGTH: 20
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 91

Trp Ile Gly Trp Ile Asp Pro Glu Asn Gly Asp Thr Glu Tyr Ala Ser
1               5                   10                  15

Lys Phe Gln Gly
            20

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Leu Val His Leu Arg Thr Phe Ala Tyr
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ala Ser Glu Ser Val Asp Ser Tyr Asp Asn Ser Leu His
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Ala Ser Asn Leu Glu Ser
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Asn Asn Glu Asp Pro Trp Thr
1               5

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 96

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Asp
            20                  25                  30

Tyr Leu His Trp Val Lys Gln Ala Pro Gly Gln Gly Leu Glu Trp Ile
        35                  40                  45

Gly Trp Ile Asp Pro Glu Asn Gly Asp Thr Gly Tyr Ala Ser Lys Phe
    50                  55                  60

Gln Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Pro Leu Val His Leu Arg Thr Phe Ala Tyr Trp Gly Gln Gly
            100                 105                 110

Thr Thr Val Thr Val Ser Ser
        115

<210> SEQ ID NO 97
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Leu Thr Gln Ser Pro Ser Ser Leu Ser Ala Ser Val Gly
1               5                   10                  15

Asp Arg Val Thr Met Thr Cys Arg Ala Ser Glu Ser Val Asp Ser Tyr
            20                  25                  30

Asp Asn Ser Leu His Trp Phe Gln Gln Lys Pro Gly Lys Ala Pro Lys
        35                  40                  45

Pro Trp Ile Tyr Leu Ala Ser Asn Leu Glu Ser Gly Val Pro Val Arg
    50                  55                  60

Phe Ser Gly Ser Gly Ser Gly Thr Asp Tyr Thr Phe Thr Ile Ser Ser
65                  70                  75                  80

Leu Gln Pro Glu Asp Ile Ala Thr Tyr Tyr Cys Gln Gln Asn Asn Glu
                85                  90                  95

Asp Pro Trp Thr Phe Gly Gly Gly Thr Lys Leu Glu Ile Lys Arg
            100                 105                 110

<210> SEQ ID NO 98
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Leu His Trp Val Lys Gln Arg Pro Glu Gln Gly Leu Glu Trp Ile
        35                  40                  45
```

-continued

```
Gly Trp Ile Asp Pro Glu Asn Gly Asp Thr Glu Tyr Ala Ser Lys Phe
 50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ser Ser Pro Leu Val His Leu Arg Thr Phe Ala Tyr Trp Gly Gln Gly
            100                 105                 110

Thr Leu Val Thr Val Ser
        115
```

<210> SEQ ID NO 99
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Asp Ile Gln Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Asp Asn Ser Leu His Trp Phe Gln Gln Lys Pro Gly Gln Pro Pro Lys
         35                  40                  45

Leu Leu Ile Tyr Leu Ala Ser Asn Leu Glu Ser Gly Val Pro Ala Arg
 50                  55                  60

Phe Ser Gly Ser Gly Ser Arg Thr Asp Phe Thr Leu Thr Ile Asp Pro
 65                  70                  75                  80

Val Glu Ala Asp Asp Ala Ala Thr Tyr Tyr Cys Gln Gln Asn Asn Glu
                 85                  90                  95

Asp Pro Trp Thr Phe Gly Gly Gly Thr Lys Leu Glu Ile Lys Arg
            100                 105                 110
```

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Ser Tyr Trp Met His
 1               5
```

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

```
Asn Ile Asp Pro Ser Asp Ser Glu Thr His Tyr Asn Gln Lys Phe Lys
 1               5                  10                  15

Asp
```

```
<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Lys Ile Thr Asp Asp Tyr Asn Tyr Phe Asp Tyr
1               5                   10

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Ala Ser Glu Ser Val Asp Ser Tyr Gly Asn Ser Phe Met His
1               5                   10                  15

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

His Ala Ser Asn Leu Glu Ser
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Asn Asn Glu Asp Pro Leu Thr
1               5

<210> SEQ ID NO 106
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Glu Trp Ile
        35                  40                  45

Gly Asn Ile Asp Pro Ser Asp Ser Glu Thr His Tyr Asn Gln Lys Phe
    50                  55                  60
```

```
Lys Asp Lys Ala Thr Leu Thr Ala Asp Glu Ser Thr Asn Thr Ala Tyr
 65                  70                  75                  80

Met Glu Leu Ser Ser Leu Arg Ser Glu Asp Thr Ala Phe Tyr Tyr Cys
                 85                  90                  95

Ala Arg Glu Lys Ile Thr Asp Asp Tyr Asn Tyr Phe Asp Tyr Trp Gly
            100                 105                 110

Gln Gly Thr Thr Val Thr Val Ser Ser
        115                 120

<210> SEQ ID NO 107
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Leu Thr Gln Ser Pro Ser Ser Leu Ser Ala Ser Val Gly
 1               5                  10                  15

Asp Arg Val Thr Met Thr Cys Arg Ala Ser Glu Ser Val Asp Ser Tyr
                20                  25                  30

Gly Asn Ser Phe Met His Trp Phe Gln Gln Lys Pro Gly Lys Ala Pro
            35                  40                  45

Lys Pro Trp Ile Tyr His Ala Ser Asn Leu Glu Ser Gly Val Pro Val
 50                  55                  60

Arg Phe Ser Gly Ser Gly Ser Gly Thr Asp Thr Phe Thr Ile Ser
 65                  70                  75                  80

Ser Leu Gln Pro Glu Asp Ile Ala Thr Tyr Tyr Cys Gln Gln Asn Asn
                 85                  90                  95

Glu Asp Pro Leu Thr Phe Gly Gly Gly Thr Lys Leu Glu Ile Lys Arg
            100                 105                 110

<210> SEQ ID NO 108
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Gln Glu Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asp Pro Ser Asp Ser Glu Thr His Tyr Asn Gln Lys Phe
 50                  55                  60

Lys Asp Lys Ala Thr Leu Thr Val Asp Lys Ser Ser Asn Thr Ala Tyr
 65                  70                  75                  80

Met Gln Leu Ser Ser Leu Thr Ser Glu Asp Ser Ala Val Phe Tyr Cys
                 85                  90                  95

Ala Arg Glu Lys Ile Thr Asp Asp Tyr Asn Tyr Phe Asp Tyr Trp Gly
            100                 105                 110

Gln Gly Thr Thr Leu Thr Val Ser
        115                 120
```

```
<210> SEQ ID NO 109
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Leu Thr Gln Ser Pro Ala Ser Leu Ala Leu Ser Leu Arg
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr His Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Tyr Val Met Tyr
1               5

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Ile Asn Pro Tyr Asn Asp Gly Thr Lys Tyr Asn Glu Lys Phe Lys
1               5                   10                  15

Gly

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Pro Gly Asp Gly Tyr Pro Phe Asp Tyr
1               5
```

```
<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Ser Ser Gln Ser Ile Val His Ser Asn Gly Asn Thr Tyr Leu Glu
1               5                   10                  15

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Val Ser Asn Arg Phe Ser
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Phe Gln Gly Ser His Val Pro Tyr Thr
1               5

<210> SEQ ID NO 116
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Val Met Tyr Trp Val Lys Gln Ala Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Pro Gly Asp Gly Tyr Pro Phe Asp Tyr Trp Gly Gln Gly Thr
            100                 105                 110

Thr Val Thr Val Ser Ser
        115
```

```
<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Gln Leu Thr Gln Ser Pro Ser Leu Ser Ala Ser Val Gly
1               5                   10                  15

Asp Arg Val Thr Met Thr Cys Arg Ser Ser Gln Ser Ile Val His Ser
            20                  25                  30

Asn Gly Asn Thr Tyr Leu Glu Trp Phe Gln Gln Lys Pro Gly Lys Ala
        35                  40                  45

Pro Lys Pro Trp Ile Tyr Lys Val Ser Asn Arg Phe Ser Gly Val Pro
    50                  55                  60

Val Arg Phe Ser Gly Ser Gly Ser Gly Thr Asp Tyr Thr Phe Thr Ile
65                  70                  75                  80

Ser Ser Leu Gln Pro Glu Asp Ile Ala Thr Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 118
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Lys Leu Gln Gln Ser Gly Pro Glu Leu Val Lys Pro Gly Ala
1               5                   10                  15

Ser Val Lys Met Ser Cys Arg Ala Ser Gly Tyr Thr Phe Thr Ser Tyr
            20                  25                  30

Val Met Tyr Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Gly Pro Gly Asp Gly Tyr Pro Phe Asp Tyr Trp Gly Gln Gly Thr
            100                 105                 110

Thr Leu Thr Val Ser
        115

<210> SEQ ID NO 119
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 119

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Ser Gly Thr Lys Leu Glu Ile Lys
            100                 105                 110

Arg

<210> SEQ ID NO 120
<211> LENGTH: 118
<212> TYPE: PRT
<213> ORGANISM: Mus musculus
<220> FEATURE:
<221> NAME/KEY: MOD_RES
<222> LOCATION: (13)..(14)
<223> OTHER INFORMATION: Any amino acid

<400> SEQUENCE: 120

Glu Ile Gln Leu Gln Gln Ser Gly Ala Glu Leu Val Xaa Xaa Gly Ala
1               5                   10                  15

Ser Val Lys Leu Ser Cys Thr Ala Ser Gly Phe Asn Ile Lys Asp Asp
            20                  25                  30

Tyr Leu His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Ser Pro Leu Val His Leu Arg Thr Phe Ala Tyr Trp Gly Gln Gly
            100                 105                 110

Thr Leu Val Thr Val Ser
        115

<210> SEQ ID NO 121
<211> LENGTH: 95
<212> TYPE: PRT
<213> ORGANISM: Mus musculus

<400> SEQUENCE: 121

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

```
Asp Asn Ser Leu His Trp Phe Gln Gln Lys Pro Gly Gln Pro Pro Lys
            35                  40                  45

Leu Leu Ile Tyr Leu Ala Ser Asn Leu Glu Ser Gly Val Pro Ala Arg
 50                      55                  60

Phe Ser Gly Ser Gly Ser Arg Thr Asp Phe Thr Leu Thr Ile Asp Pro
 65                  70                  75                  80

Val Glu Ala Asp Asp Ala Ala Thr Tyr Tyr Cys Gln Gln Asn Asn
                 85                  90                  95

<210> SEQ ID NO 122
<211> LENGTH: 120
<212> TYPE: PRT
<213> ORGANISM: Mus musculus

<400> SEQUENCE: 122

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Asn Ile Asp Pro Ser Asp Ser Glu Thr His Tyr Asn Gln Lys Phe
     50                  55                  60

Lys Asp Lys Ala Thr Leu Thr Val Asp Lys Ser Ser Asn Thr Ala Tyr
 65                  70                  75                  80

Met Gln Leu Ser Ser Leu Thr Ser Glu Asp Ser Ala Val Phe Tyr Cys
                 85                  90                  95

Ala Arg Glu Lys Ile Thr Asp Asp Tyr Asn Tyr Phe Asp Tyr Trp Gly
             100                 105                 110

Gln Gly Thr Thr Leu Thr Val Ser
         115                 120

<210> SEQ ID NO 123
<211> LENGTH: 91
<212> TYPE: PRT
<213> ORGANISM: Mus musculus

<400> SEQUENCE: 123

Lys Ile Val Leu Thr Gln Ser Pro Ala Ser Leu Ala Leu Ser Leu Arg
 1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr His Ala Ser Asn Leu Glu Ser Gly Val Pro Ala
     50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr
                 85                  90

<210> SEQ ID NO 124
<211> LENGTH: 117
<212> TYPE: PRT
<213> ORGANISM: Mus musculus
```

```
<400> SEQUENCE: 124

Glu Val Gln Leu Gln Gln Ser Gly Pro Glu Leu Val Arg Pro Gly Ala
1               5                   10                  15

Ser Val Lys Met Ser Cys Arg Ala Ser Gly Tyr Thr Phe Thr Ser Tyr
            20                  25                  30

Val Met Tyr Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Gly Pro Gly Asp Gly Tyr Pro Phe Asp Tyr Trp Gly Gln Gly Thr
            100                 105                 110

Thr Leu Thr Val Ser
        115

<210> SEQ ID NO 125
<211> LENGTH: 91
<212> TYPE: PRT
<213> ORGANISM: Mus musculus
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (72)..(72)
<223> OTHER INFORMATION: Any amino acid

<400> SEQUENCE: 125

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Xaa Lys Pro Gly Gln Ser
        35                  40                  45

Pro Lys Leu Leu Ile Tyr Lys Val Ser Asn Arg Phe Ser Xaa Val Pro
    50                  55                  60

Asp Arg Phe Ser Gly Ser Gly Xaa Gly Thr Asp Phe Thr Leu Lys Ile
65                  70                  75                  80

Ser Arg Val Glu Ala Glu Asp Leu Gly Val Tyr
                85                  90

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Glu Phe Pro Lys Pro Ser Thr Pro Pro Gly Ser Ser Gly Gly Ala Pro
1               5                   10                  15
```

<210> SEQ ID NO 127
<211> LENGTH: 327
<212> TYPE: PRT
<213> ORGANISM: Homo sapiens

<400> SEQUENCE: 127

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 128
<211> LENGTH: 106
<212> TYPE: PRT
<213> ORGANISM: Homo sapiens

```
<400> SEQUENCE: 128

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

CHIMERIC AND HUMANIZED ANTI-HISTONE ANTIBODIES

RELATED APPLICATIONS

This application is a divisional of U.S. patent application Ser. No. 15/713,031, filed Sep. 22, 2017, which was a divisional of U.S. patent application Ser. No. 15/487,747 (now issued U.S. Pat. No. 9,809,646), filed Apr. 14, 2017, which was a divisional of U.S. patent application Ser. No. 15/005,596 (now issued U.S. Pat. No. 9,657,093), filed Jan. 25, 2016, which was a divisional of U.S. patent application Ser. No. 14/620,315 (now issued U.S. Pat. No. 9,278,129), filed Feb. 12, 2015, which was a divisional of U.S. patent application Ser. No. 14/180,646 (now issued U.S. Pat. No. 8,987,421), filed Feb. 14, 2014, which claimed the benefit under 35 U.S.C. 119(e) of provisional U.S. Patent Application Ser. No. 61/765,150, filed Feb. 15, 2013.

SEQUENCE LISTING

The instant application contains a Sequence Listing which has been submitted in ASCII format via EFS-Web and is hereby incorporated by reference in its entirety. Said ASCII copy, created on Feb. 10, 2014, is named IMM342US1_SL.txt and is 71,342 bytes in size.

FIELD OF THE INVENTION

The invention relates to compositions and methods of use of anti-histone antibodies or antigen-binding fragments thereof. In particular embodiments, the antibodies bind to human histones H2B, H3 or H4. The anti-histone antibodies are of use for diagnosis and/or therapy of a wide range of disease states, including but not limited to, autoimmune disease (such as systemic lupus erythematosus), atherosclerosis, arthritis, rheumatoid arthritis, juvenile arthritis; edema; sepsis; septic shock; inflammation; non-septic hyperinflammatory disorder; infectious disease; thrombosis; nephritis; inflammatory liver injury; traumatic hemorrhage; acute pancreatitis; acute respiratory distress syndrome; ischemic injury; ischemia-reperfusion injury; ischemic stroke; cardiovascular disease; atherosclerosis; radiotherapy toxicity; cytokine therapy toxicity; granulomatous disease; asthma; graft-vs.-host disease, cachexia, a coagulopathy; cancer; or burn effects and complications thereof. More particular embodiments may concern chimeric or more preferably humanized forms of the anti-histone antibodies.

BACKGROUND

Sepsis is a major medical and economic burden to our society, affecting about 700,000 people annually in the United States, causing over 200,000 deaths annually, and costing approximately $16.7 billion per year (Angus et al., *Crit Care Med* 2001; 29:1303-1310; Martin et al., *N Engl J Med* 2003; 348:1546-1554). The definition of sepsis has been difficult, and historically it was defined as the systemic host response to an infection. A discussion of the clinical definition of sepsis, encompassing systemic inflammatory response syndrome (SIRS), sepsis per se, severe sepsis, septic shock, and multiple organ dysfunction syndrome (MODS) is contained in Riedmann et al., *J Clin Invest* 2003; 112:460-467. Since it has been a common belief that sepsis is caused by the host's overwhelming reaction to the invading microorganisms, and that the patient is more endangered by this response than the invading microorganisms, suppression of the immune and inflammatory responses was an early goal of therapy.

Numerous and diverse methods of immunosuppression or of neutralizing proinflammatory cytokines have proven to be unsuccessful clinically in patients with sepsis and septic shock anti-inflammatory strategies. (*J Clin Invest* 2003; 112:460-467; Van Amersfoort et al. (*Clin Microbial Rev* 2003; 16:379-414), such as general immunosuppression, use of nonsteroidal anti-inflammatory drugs, TNF-α antibody (infliximab) or a TNF-R:Fc fusion protein (etanercept), IL-1 (interleukin-1) receptor antagonist, or high doses of corticosteroids. However, a success in the treatment of sepsis in adults was the PROWESS study (Human Activated Protein C Worldwide Evaluation in Severe Sepsis (Bernard et al., *N Engl J Med* 2001; 344:699-709)), showing a lower mortality (24.7%) than in the placebo group (30.8%). This activated protein C (APC) agent probably inhibits both thrombosis and inflammation, whereas fibrinolysis is fostered. Friggeri et al. (2012, *Mol Med* 18:825-33) reported that APC degrades histones H3 and H4, which block uptake and clearance of apoptotic cells by macrophages and thereby contribute to organ system dysfunction and mortality in acute inflammatory states. Van Amersfoort et al. state, in their review (ibid.) that: "Although the blocking or modulation of a number of other targets including complement and coagulation factors, neutrophil adherence, and NO release, are promising in animals, it remains to be determined whether these therapeutic approaches will be effective in humans." This is further emphasized in a review by Abraham, "Why immunomodulatory therapies have not worked in sepsis" (*Intensive Care Med* 1999; 25:556-566). In general, although many rodent models of inflammation and sepsis have shown encouraging results with diverse agents over the past decade or more, most agents translated to the clinic failed to reproduce in humans what was observed in these animal models, so that there remains a need to provide new agents that can control the complex presentations and multiple-organ involvement of various diseases involving sepsis, coagulopathy, and certain neurodegenerative conditions having inflammatory or immune dysregulatory components.

More recent work on immunoglobulins in sepsis or septic shock has been reported. For example, Toussaint and Gerlach (2012, *Curr Infect Dis Rep* 14:522-29) summarized the use of ivIG as an adjunct therapy in sepsis. The metanalysis failed to show any strong correlation between general immunoglobulin therapy and outcome. LaRosa and Opal (2012, *Curr Infect Dis Rep* 14:474-83) reported on new therapeutic agents of potential use in sepsis. Among other agents, anti-TNF antibodies are in current clinical trials for sepsis, while complement antagonists have shown promising results in preclinical models of sepsis. Nalesso et al. (2012, *Curr Infect Dis Rep* 14:462-73) suggested that combination therapies with multiple agents may prove more effective for sepsis treatment. The immunopathogenesis of sepsis has been summarized by Cohen (2002, *Nature* 420:885-91).

The immune system in sepsis is believed to have an early intense proinflammatory response after infection or trauma, leading to organ damage, but it is also believed that the innate immune system often fails to effectively kill invading microorganisms (Riedmann and Ward, *Expert Opin Biol Ther* 2003; 3:339-350). There have been some studies of macrophage migration inhibitory factor (MIF) in connection with sepsis that have shown some promise. For example, blockage of MIF or targeted disruption of the MIF gene significantly improved survival in a model of septic shock in mice (Calandra et al., *Nature Med* 2000; 6:164-170), and several lines of evidence have pointed to MIF as a potential target for therapeutic intervention in septic patients (Riedmann et al., cited above). Bucala et al. (U.S. Pat. No. 6,645,493 B1) have claimed that an anti-MIF antibody can be effective therapeutically for treating a condition or disease caused by cytokine-mediated toxicity, including different forms of sepsis, inflammatory diseases, acute respiratory disease syndrome, granulomatous diseases, chronic infections, transplant rejection, cachexia, asthma, viral infections, parasitic infections, malaria, and bacterial infections, which is incorporated herein in its entirety, including references. The use of anti-LPS (lipopolysaccharide) antibodies alone similarly has had mixed results in the treatment of patients with septic shock (Astiz and Rackow, *Lancet* 1998; 351: 1501-1505; Van Amersfoort et al., *Clin Microbiol Rev* 2003; 16:379-414.

While both LPS and MIF have been pursued as targets in the treatment of sepsis and septic shock, approaches which target LPS or MIF alone by an antibody have not been sufficient to control the diverse manifestations of sepsis, especially in advanced and severe forms. Similarly, use of cytokines, such as IL-1, IL-6 (interleukin-6), IL-8 (interleukin-8), etc., as targets for antibodies for the treatment of sepsis and other cytokine-mediated toxic reactions, has not proven to be sufficient for a meaningful control of this disease. Therefore, in addition to the need to discover additional targets of the cytokine cascade involved in the endogenous response in sepsis, it has now been discovered that bi- and multi-functional antibodies targeting at least one cytokine or causative agent, such as MIF or lipopolysaccharide (LPS), is advantageous, especially when combined with the binding to a host cell (or its receptor) engaged in the inflammatory or immune response, such as T cells, macrophages or dendritic cells. Antibodies against an MHC class II invariant chain target, such as CD74, have been proposed by Bucala et al. (US 2003/0013122 A1), for treating MIF-regulated diseases, and Hansen et al. (US 2004/0115193 A1) proposed at least one CD74 antibody for treating an immune dysregulation disease, an autoimmune disease, organ graft rejection, and graft-versus-host disease. Hansen et al. describe the use of fusion proteins of anti-CD74 with other antibodies reacting with antigens/receptors on host cells such as lymphocytes and macrophages for the treatment of such diseases. However, combinations with targets other than CD74 are not suggested, and the disclosure focuses on a different method of immunotherapy. Similar targets are also useful to treat atherosclerotic plaques (Burger-Kentischer et al., *Circulation* 2002; 105:1561-1566).

In the treatment of infectious, autoimmune, organ transplantation, inflammatory, and graft-versus-host (and other immunoregulatory) diseases, diverse and relatively non-specific cytotoxic agents are used to either kill or eliminate the noxient or microorganism, or to depress the host's immune response to a foreign graft or immunogen, or the host's production of antibodies against "self," etc. However, these usually affect the lymphoid and other parts of the hematopoietic system, giving rise to toxic effects to the bone marrow (hematopoietic) and other normal host cells. Particularly in sepsis, where an immunosuppressed status is encountered, use of immunosuppressive therapies would be counter-indicated, so it is a goal to effect a careful balance between targeting and inhibiting key cells of the adaptive immune system while not depleting those involved with the host maintaining an active immune system.

A need exists for improved, more selective therapy of cancer and diverse immune diseases, including sepsis and septic shock, inflammation, atherosclerosis, cachexia, graft-versus-host, and other immune dysregulatory disorders.

SUMMARY

Certain embodiments concern chimeric or humanized versions of antibodies against histones, such as IMMU-H4, IMMU-H3 or IMMU-H2B. The amino acid sequences of the variable region domains of the IMMU-H4, IMMU-H3 and IMMU-H2B antibodies were determined by DNA sequencing. Chimeric antibodies were designed and constructed by replacing murine constant region sequences with human antibody constant region sequences. Humanized antibodies are designed and constructed by inserting the identified CDR sequences into human antibody framework region (FR) sequences, attached to human antibody constant region sequences. In preferred embodiments, selected human FR amino acid residues are replaced with the corresponding murine FR residues from the parental murine antibody, to optimize binding or other activities of the humanized antibody.

The chimeric and/or humanized anti-histone antibodies or antigen-binding fragments thereof are of use for diagnosis and/or therapy of a wide range of disease states, including but not limited to, autoimmune disease, such as systemic lupus erythematosus (SLE), autoimmune disease other than SLE, atherosclerosis, arthritis, rheumatoid arthritis, juvenile arthritis; edema; sepsis; septic shock; inflammation; a non-septic hyperinflammatory disorder; infectious disease; thrombosis; nephritis; inflammatory liver injury; traumatic hemorrhage; acute pancreatitis; acute respiratory distress syndrome; ischemic injury; ischemia-reperfusion injury; ischemic stroke; cardiovascular disease; atherosclerosis; radiotherapy toxicity; cytokine therapy toxicity; granulomatous disease; asthma; graft-vs.-host disease, cachexia, a coagulopathy; cancer; or burn effects and complications.

In certain preferred embodiments, a combination of anti-histone antibodies may be used. Antibodies against human histones H1, H2A, H2B, H3 or H4 may be used in any combination. Other non-antibody therapeutic agents targeted against either histones or downstream effectors of a histone-mediated pathway may also be utilized in combination with anti-histone antibodies or fragments thereof, administered either before, simultaneously with, or following administration of one or more anti-histone antibodies or fragments thereof. Various therapeutic agents of use in treating histone-associated disease states are known in the art, such as activated protein C (APC), thrombomodulin, a peptide fragment of histone H1, H2A, H2B, H3 or H4, granzyme A, granzyme B, plasmin, Factor 7-activating protease, heparin, and any such known agent may be utilized in combination with the subject anti-histone antibodies or antibody fragments. A human histone H4 peptide may comprise residues 50-67 or 40-78 of human H4 (see, e.g., U.S. Publ. No. 20090117099).

In alternative embodiments, the disclosed methods and/or compositions may utilize one or more chimeric, humanized or human antibodies or antigen-binding antibody fragments that compete for binding with, or bind to the same epitope as, an IMMU-H4, IMMU-H3 or IMMU-H2B antibody. These can be combined with agents affecting or inhibiting the innate or adaptive immune systems (including proinflammatory effector cytokines or a proinflammatory effector chemokines; regulatory T cells and other hematopoietic cells implicated in the disease); the complement system, and/or a coagulation factor or factors that contribute to the pathology or pathogenesis of the disease. These combinations or multispecific agents, including multispecific antibodies, are intended to enhance the effects of anti-histone antibodies in the management of these diverse diseases.

Specific embodiments concern chimeric and humanized antibodies of particular allotypes. Preferably, the antibody constant region sequences are selected to correspond to an nG1m1,2 heavy chain null allotype, more preferably a G1m3 heavy chain allotype, more preferably a Km3 light chain allotype.

Surprisingly, it is discovered that the chimeric and humanized forms of the anti-histone antibodies may exhibit a higher affinity for the target histones than the parent murine antibodies.

BRIEF DESCRIPTION OF THE DRAWINGS

The following drawings are provided to illustrate preferred embodiments of the invention. However, the claimed subject matter is in no way limited by the illustrative embodiments disclosed in the drawings.

FIG. 1. Comparison of the variable region amino acid sequences of the murine IMMU-H4 heavy and light chains with the corresponding sequences published by Monestier et al. (1993, Mol. Immunol 30:1069-75) for the BWA-3 antibody. Underlined residues show discrepancies. "X" indicates a residue missing from the published sequence. The correct amino acid sequences of murine IMMU-H4 heavy chain (SEQ ID NO:98) and light chain (SEQ ID NO:99) are shown alongside the incorrect published sequences of murine BWA-3 heavy chain (SEQ ID NO:120) and light chain (SEQ ID NO:121)

FIG. 2. Comparison of the variable region amino acid sequences of the murine IMMU-H3 heavy and light chains with the corresponding sequences published in Monestier et al. (1993, *Mol. Immunol* 30:1069-75) for the LG2-1 antibody. Underlined residues show discrepancies. "X" indicates a residue missing from the published sequence. The correct amino acid sequences of murine IMMU-H3 heavy chain (SEQ ID NO:108) and light chain (SEQ ID NO:109) are shown alongside the incorrect published sequences of murine LG2-1 heavy chain (SEQ ID NO:122) and light chain (SEQ ID NO:123)

FIG. 3. Comparison of the variable region amino acid sequences of the murine IMMU-H2B heavy and light chains with the corresponding sequences published in Monestier et al. (1993, *Mol. Immunol* 30:1069-75) for the LG2-2 antibody. Underlined residues show discrepancies. "X" indicates a residue missing from the published sequence. The correct amino acid sequences of murine IMMU-H2B heavy chain (SEQ ID NO:118) and light chain (SEQ ID NO:119) are shown alongside the incorrect published sequences of murine LG2-2 heavy chain (SEQ ID NO:124) and light chain (SEQ ID NO:125)

FIG. 4. Amino acid sequences of the heavy chain (SEQ ID NO:96) and light chain (SEQ ID NO:97) variable regions of the humanized IMMU-H4 antibody. Residues that differ from the murine parent antibody are underlined.

FIG. 5. Amino acid sequences of the heavy chain (SEQ ID NO:106) and light chain (SEQ ID NO:107) variable regions of the humanized IMMU-H3 antibody. Residues that differ from the murine parent antibody are underlined.

FIG. 6. Amino acid sequences of the heavy chain (SEQ ID NO:116) and light chain (SEQ ID NO:117) variable regions of the humanized IMMU-H2B antibody. Residues that differ from the murine parent antibody are underlined.

DEFINITIONS

Figure 7:
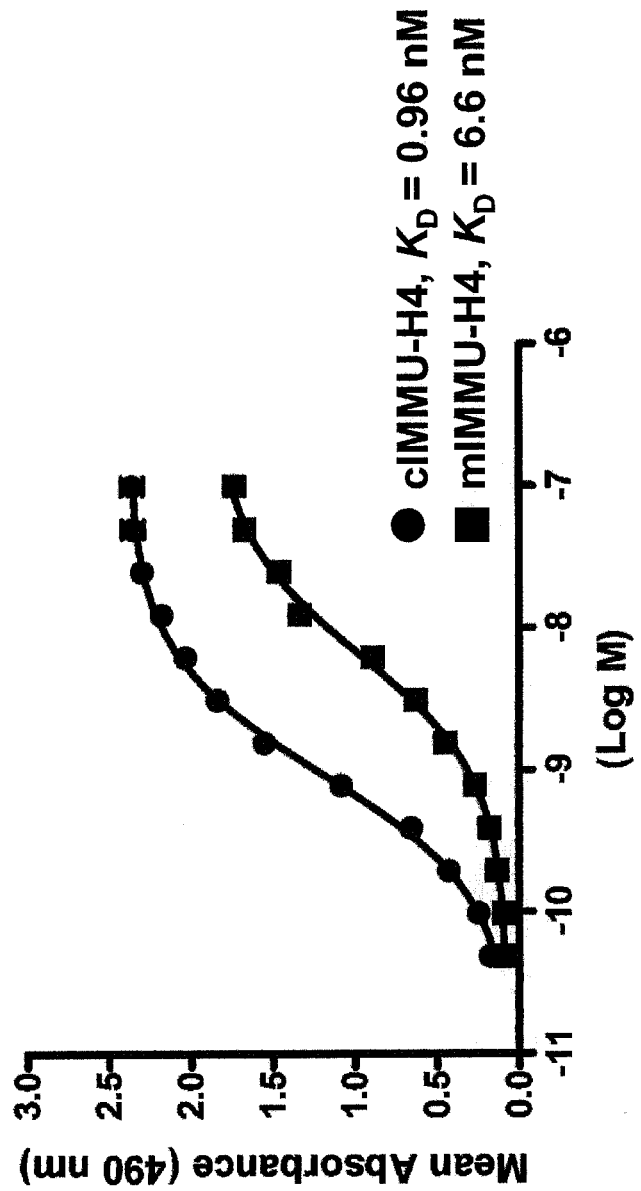
FIG. 7. Comparative binding affinities of murine (squares) and chimeric (circles) IMMU-H4 anti-histone antibodies.

Unless otherwise specified, "a" or "an" means "one or more".

As used herein, the terms "and" and "or" may be used to mean either the conjunctive or disjunctive. That is, both terms should be understood as equivalent to "and/or" unless otherwise stated.

A "therapeutic agent" is an atom, molecule, or compound that is useful in the treatment of a disease. Examples of therapeutic agents include antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes.

A "diagnostic agent" is an atom, molecule, or compound that is useful in diagnosing a disease. Useful diagnostic agents include, but are not limited to, radioisotopes, dyes (such as with the biotin-streptavidin complex), contrast agents, fluorescent compounds or molecules, and enhancing agents (e.g., paramagnetic ions) for magnetic resonance imaging (MRI).

An "antibody" as used herein refers to a full-length (i.e., naturally occurring or formed by normal immunoglobulin gene fragment recombinatorial processes) immunoglobulin molecule (e.g., an IgG antibody). An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as F(ab')$_2$, F(ab)$_2$, Fab', Fab, Fv, sFv, scFv, dAb and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb). Fragments of antibodies that do not bind to the same antigen as the intact antibody, such as the Fc fragment, are not included within the scope of an "antibody fragment" as used herein.

An anti-histone antibody or antibody fragment, or a composition described herein, is said to be administered in a "therapeutically effective amount" if the amount administered is physiologically significant. An agent is physiologically significant if its presence results in a detectable change in the physiology of a recipient subject. In particular embodiments, an antibody preparation is physiologically significant if its presence invokes an antitumor response or mitigates the signs and symptoms of an autoimmune disease state. A physiologically significant effect could also be the evocation of a humoral and/or cellular immune response in the recipient subject leading to growth inhibition or death of target cells.

Anti-Histone Antibodies

Various humanized or chimeric anti-histone antibodies and/or antigen-binding fragments thereof are disclosed herein. The murine BWA-3 (anti-H4), LG2-1 (anti-H3) and LG2-2 (anti-H2B) hybridomas from which the currently disclosed chimeric and humanized IMMU-H4, IMMU-H3 and IMMU-H2B antibodies were derived were reported by Monestier et al. (1993, *Mol. Immunol* 30:1069-75). However, murine antibodies are generally not appropriate for human therapeutic use, due to the formation of human anti-mouse antibodies (HAMA) that can neutralize these antibodies and thus make them less active. Further, the variable region sequences reported by Monestier et al. (1993) for murine BWA-3, LG2-1 and LG2-2 were incorrect and/or incomplete and could not have provided the basis for production of chimeric or humanized antibodies.

In preferred embodiments, a humanized or chimeric IMMU-H4 antibody is one that comprises the heavy chain complementarity-determining region (CDR) sequences CDR1 (DDYLH, SEQ ID NO:90), CDR2 (WIGWID-PENGDTEYASKFQG, SEQ ID NO:91) and CDR3 (PLVHLRTFAY, SEQ ID NO:92) and the light chain CDR sequences CDR1 (RASESVDSYDNSLH, SEQ ID NO:93), CDR2 (LASNLES, SEQ ID NO:94) and CDR3 (QQNNED-PWT, SEQ ID NO:95). In more preferred embodiments, the humanized IMMU-H4 antibody comprises the heavy and light chain variable region sequences of SEQ ID NO:96 and SEQ ID NO:97. In other preferred embodiments, the chimeric IMMU-H4 antibody comprises the heavy and light chain variable region sequences of SEQ ID NO:98 and SEQ ID NO:99.

Humanized IMMU-H4 VH Sequence
(SEQ ID NO: 96)
QVQLQQSGAEVKKPGSSVKVSCKASGYTFTDDYLHWVKQAPGQGLEWIGW

IDPENGDTEYASKFQGKATLTADESTNTAYMELSSLRSEDTAFYYCARPL

VHLRTFAYWGQGTTVTVSS

Humanized IMMU-H4 VK Sequence
(SEQ ID NO: 97)
DIQLTQSPSSLSASVGDRVTMTCRASESVDSYDNSLHWFQQKPGKAPKPW

IYLASNLESGVPVRFSGSGSGTDYTFTISSLQPEDIATYYCQQNNEDPWT

FGGGTKLEIKR

Chimeric IMMU-H4 VH Sequence
(SEQ ID NO: 98)
QVQLQQSGAELVRPGASVKLSCTASGFNIKDDYLHWVKQRPEQGLEWIGW

IDPENGDTEYASKFQGKATITADTSSNTAYLQLSSLTSEDTAVYYCSSPL

VHLRTFAYWGQGTLVTVS

Chimeric IMMU-H4 VK Sequence
(SEQ ID NO: 99)
DIQLTQSPASLAVSLGQRATISCRASESVDSYDNSLHWFQQKPGQPPKLL

IYLASNLESGVPARFSGSGSRTDFTLTIDPVEADDAATYYCQQNNEDPWT

FGGGTKLEIKR

In preferred embodiments, a humanized or chimeric IMMU-H3 antibody is one that comprises the heavy chain CDR sequences CDR1 (SYWMH, SEQ ID NO:100), CDR2 (NIDPSDSETHYNQKFKD, SEQ ID NO:101) and CDR3 (EKITDDYNYFDY, SEQ ID NO:102) and the light chain CDR sequences CDR1 (RASESVDSYGNSFMH, SEQ ID NO:103), CDR2 (HASNLES, SEQ ID NO:104) and CDR3 (QQNNEDPLT, SEQ ID NO:105). In more preferred embodiments, the humanized IMMU-H3 antibody comprises the heavy and light chain variable region sequences of SEQ ID NO:106 and SEQ ID NO:107. In other preferred embodiments, the chimeric IMMU-H3 antibody comprises the heavy and light chain variable region sequences of SEQ ID NO:108 and SEQ ID NO:109.

Humanized IMMU-H3 VH Sequence
(SEQ ID NO: 106)
QVQLQQSGAEVKKPGSSVKVSCKASGYTFTSYWMHWVKQAPGQGLEWIGN

IDPSDSETHYNQKFKDKATLTADESTNTAYMELSSLRSEDTAFYYCAREK

ITDDYNYFDYWGQGTTVTVSS

Humanized IMMU-H3 VK Sequence
(SEQ ID NO: 107)
DIQLTQSPSSLSASVGDRVTMTCRASESVDSYGNSFMHWFQQKPGKAPKP

WIYHASNLESGVPVRFSGSGSGTDYTFTISSLQPEDIATYYCQQNNEDPL

TFGGGTKLEIKR

Chimeric IMMU-H3 VH Sequence
(SEQ ID NO: 108)
QVQLQESGAELVKPGASVKLSCKASGYTFTSYWMHWVKQRPGQGLEWIGN

IDPSDSETHYNQKFKDKATLTVDKSSNTAYMQLSSLTSEDSAVFYCAREK

ITDDYNYFDYWGQGTTLTVS

Chimeric IMMU-H3 VK Sequence
(SEQ ID NO: 109)
DIQLTQSPASLALSLRQRATISCRASESVDSYGNSFMHWYQQKPGQPPKL

LIYHASNLESGVPARFSGSGSRTDFTLTIDPVEADDAATYYCQQNNEDPL

TFGAGTKLELKR

In preferred embodiments, a humanized or chimeric IMMU-H2B antibody is one that comprises the heavy chain CDR sequences CDR1 (SYVMY, SEQ ID NO:110), CDR2 (YINPYNDGTKYNEKFKG, SEQ ID NO:111) and CDR3 (PGDGYPFDY, SEQ ID NO:112) and the light chain CDR sequences CDR1 (RSSQSIVHSNGNTYLE, SEQ ID NO:113), CDR2 (KVSNRFS, SEQ ID NO:114) and CDR3 (FQGSHVPYT, SEQ ID NO:115). In more preferred embodiments, the humanized IMMU-H2B antibody comprises the heavy and light chain variable region sequences of SEQ ID NO:116 and SEQ ID NO:117. In other preferred embodiments, the chimeric IMMU-H2B antibody comprises the heavy and light chain variable region sequences of SEQ ID NO:118 and SEQ ID NO:119.

Humanized IMMU-H2B VH Sequence
(SEQ ID NO: 116)
QVQLQQSGAEVKKPGSSVKVSCKASGYTFTSYVMYWVKQAPGQGLEWIGY

INPYNDGTKYNEKFKGKATLTADESTNTAYMELSSLRSEDTAFYYCARPG

DGYPFDYWGQGTTVTVSS

Humanized IMMU-H2B VK Sequence
(SEQ ID NO: 117)
DIQLTQSPSSLSASVGDRVTMTCRSSQSIVHSNGNTYLEWFQQKPGKAPK

PWIYKVSNRFSGVPVRFSGSGSGTDYTFTISSLQPEDIATYYCFQGSHVP

YTFGGGTKLEIKR

-continued

Chimeric IMMU-H2B VK Sequence
(SEQ ID NO: 118)
QVKLQQSGPELVKPGASVKMSCRASGYTFTSYVMYWVKQKPGQGLEWIGY

INPYNDGTKYNEKFKGKATLTSDKSSTAYMELSSLTSEDSAVYYCAGPG

DGYPFDYWGQGTTLTVS

Chimeric IMMU-H2B VK Sequence
(SEQ ID NO: 119)
DVLMTQTPLSLPVSLGDQASISCRSSQSIVHSNGNTYLEWYLQKPGQSPK

LLIYKVSNRFSGVPDRFSGSGSGTDFTLKISRVEAEDLGVYYCFQGSHVP

YTFGSGTKLEIKR

General Techniques for Antibodies and Antibody Fragments

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., Biotechnology 9:266 (1991) and Verhoeyen et al., Science 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Phamacol. 3:544-50). A fully human antibody also can be constructed by genetic or chromosomal transfection methods, as well as phage display technology, all of which are known in the art. See for example, McCafferty et al., Nature 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, Genet. Mol. Res. 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, J. Mol. Biol. 222:581-97). Library construction was performed according to Andris-Widhopf et al. (2000, In: Phage Display Laboratory Manual, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, Nature 380:364-366; Pasqualini, 1999, The Quart. J. Nucl. Med. 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as F(ab')$_2$, Fab', F(ab)$_2$, Fab, Fv, sFv and the like. F(ab')$_2$ fragments can be produced by pepsin digestion of the antibody molecule and Fab' fragments can be generated by reducing disulfide bridges of the F(ab')$_2$ fragments. Alternatively, Fab' expression libraries can be constructed (Huse et al., 1989, *Science*, 246:1274-1281) to allow rapid and easy identification of monoclonal Fab' fragments with the desired specificity. F(ab)$_2$ fragments may be generated by papain digestion of an antibody.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions,*" TIBTECH, Vol 9: 132-137 (1991).

Techniques for producing single domain antibodies are also known in the art, as disclosed for example in Cossins et al. (2006, Prot Express Purif 51:253-259), incorporated herein by reference. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). In certain embodiments, anti-pancreatic cancer VHH antibody fragments may be utilized in the claimed compositions and methods.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056, 509; 7,049,060; 7,045,132; 7,041,803; 7,041,802; 7,041, 293; 7,038,018; 7,037,498; 7,012,133; 7,001,598; 6,998, 468; 6,994,976; 6,994,852; 6,989,241; 6,974,863; 6,965, 018; 6,964,854; 6,962,981; 6,962,813; 6,956,107; 6,951, 924; 6,949,244; 6,946,129; 6,943,020; 6,939,547; 6,921, 645; 6,921,645; 6,921,533; 6,919,433; 6,919,078; 6,916, 475; 6,905,681; 6,899,879; 6,893,625; 6,887,468; 6,887, 466; 6,884,594; 6,881,405; 6,878,812; 6,875,580; 6,872, 568; 6,867,006; 6,864,062; 6,861,511; 6,861,227; 6,861, 226; 6,838,282; 6,835,549; 6,835,370; 6,824,780; 6,824, 778; 6,812,206; 6,793,924; 6,783,758; 6,770,450; 6,767, 711; 6,764,688; 6,764,681; 6,764,679; 6,743,898; 6,733, 981; 6,730,307; 6,720,155; 6,716,966; 6,709,653; 6,693, 176; 6,692,908; 6,689,607; 6,689,362; 6,689,355; 6,682, 737; 6,682,736; 6,682,734; 6,673,344; 6,653,104; 6,652, 852; 6,635,482; 6,630,144; 6,610,833; 6,610,294; 6,605, 441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

Particular antibodies that may be of use for therapy of cancer within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (anti-carbonic anhydrase IX), hL243 (anti-HLA-DR), alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); rituximab (anti-CD20); tositumomab (anti-CD20); GA101 (anti-CD20); and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-α4 integrin) and omalizumab (anti-IgE).

Type-1 and Type-2 diabetes may be treated using known antibodies against B-cell antigens, such as CD22 (epratuzumab), CD74 (milatuzumab), CD19 (hA19), CD20 (veltuzumab) or HLA-DR (hL243) (see, e.g., Winer et al., 2011, Nature Med 17:610-18). Anti-CD3 antibodies also have been proposed for therapy of type 1 diabetes (Cernea et al., 2010, Diabetes Metab Rev 26:602-05).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446-54); autoimmune diseases such as rheumatoid arthritis and systemic lupus erythematosus (Morand & Leech, 2005, Front Biosci 10:12-22; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

The pharmaceutical composition of the present invention may be used to treat a subject having a metabolic disease, such amyloidosis, or a neurodegenerative disease, such as Alzheimer's disease. Bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition.

In a preferred embodiment, diseases that may be treated using the claimed compositions and methods include cardiovascular diseases, such as fibrin clots, atherosclerosis, myocardial ischemia and infarction. Antibodies to fibrin (e.g., scFv(59D8); T2G1s; MH1) are known and in clinical trials as imaging agents for disclosing said clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541,440, the Examples section of each incorporated herein by reference) Anti-macrophage, anti-low-density lipoprotein (LDL), anti-MIF, and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T-cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

Other antibodies that may be used include antibodies against infectious disease agents, such as bacteria, viruses, mycoplasms or other pathogens. Many antibodies against such infectious agents are known in the art and any such known antibody may be used in the claimed methods and compositions. For example, antibodies against the gp120 glycoprotein antigen of human immunodeficiency virus I (HIV-1) are known, and certain of such antibodies can have an immunoprotective role in humans. See, e.g., Rossi et al., Proc. Natl. Acad. Sci. USA. 86:8055-8058, 1990. Known anti-HIV antibodies include the anti-envelope antibody described by Johansson et al. (AIDS. 2006 Oct. 3; 20(15): 1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agents Chemother. 2006; 50(5):1773-9, all incorporated herein by reference.

Antibodies against malaria parasites can be directed against the sporozoite, merozoite, schizont and gametocyte stages. Monoclonal antibodies have been generated against sporozoites (cirumsporozoite antigen), and have been shown to neutralize sporozoites in vitro and in rodents (N. Yoshida et al., Science 207:71-73, 1980). Several groups have developed antibodies to *T. gondii*, the protozoan parasite involved in toxoplasmosis (Kasper et al., J. Immunol. 129:1694-1699, 1982; Id., 30:2407-2412, 1983). Antibodies have been developed against schistosomular surface antigens and have been found to act against schistosomulae in vivo or in vitro (Simpson et al., Parasitology, 83:163-177, 1981; Smith et al., Parasitology, 84:83-91, 1982: Gryzch et al., J. Immunol., 129:2739-2743, 1982; Zodda et al., J. Immunol. 129:2326-2328, 1982; Dissous et al., J. immunol., 129:2232-2234, 1982)

*Trypanosoma cruzi* is the causative agent of Chagas' disease, and is transmitted by blood-sucking reduviid insects. An antibody has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639-640, 1982).

Anti-fungal antibodies are known in the art, such as anti-Sclerotinia antibody (U.S. Pat. No. 7,910,702); antiglucuronoxylomannan antibody (Zhong and Priofski, 1998, Clin Diag Lab Immunol 5:58-64); anti-*Candida* antibodies (Matthews and Burnie, 2001, 2:472-76); and anti-glycosphingolipid antibodies (Toledo et al., 2010, BMC Microbiol 10:47).

Suitable antibodies have been developed against most of the microorganism (bacteria, viruses, protozoa, fungi, other parasites) responsible for the majority of infections in humans, and many have been used previously for in vitro diagnostic purposes. These antibodies, and newer antibodies that can be generated by conventional methods, are appropriate for use in the present invention.

Bispecific and Multispecific Antibodies

Bispecific or multispecific antibodies can be prepared by a variety of procedures, ranging from glutaraldehyde linkage to more specific linkages between functional groups. The antibodies and/or antibody fragments are preferably covalently bound to one another, directly or through a linker moiety, through one or more functional groups on the antibody or fragment, e. g., amine, carboxyl, phenyl, thiol, or hydroxyl groups. Various conventional linkers in addition to glutaraldehyde can be used, e. g., disiocyanates, diiosothiocyanates, bis (hydroxysuccinimide) esters, carbodiimides, maleimidehydroxy-succinimde esters, and the like. The optimal length of the linker may vary according to the type of target cell.

A simple method to produce multivalent antibodies is to mix the antibodies or fragments in the presence of glutaraldehyde. The initial Schiff base linkages can be stabilized, e. g., by borohydride reduction to secondary amines. A diiosothiocyanate or carbodiimide can be used in place of glutaraldehyde as a non-site-specific linker.

The simplest form of a multivalent, multispecific antibody is a bispecific antibody. Bispecific antibodies can be made by a variety of conventional methods, e. g., disulfide cleavage and reformation of mixtures of whole IgG or, preferably F (ab')$_2$ fragments, fusions of more than one hybridoma to form polyomas that produce antibodies having more than one specificity, and by genetic engineering. Bispecific antibodies have been prepared by oxidative cleavage of Fab' fragments resulting from reductive cleavage of different antibodies. This is advantageously carried out by mixing two different F (ab')$_2$ fragments produced by pepsin digestion of two different antibodies, reductive cleavage to form a mixture of Fab' fragments, followed by oxidative reformation of the disulfide linkages to produce a mixture of F (ab')$_2$ fragments including bispecific antibodies containing a Fab' portion specific to each of the original epitopes.

General techniques for the preparation of multivalent antibodies may be found, for example, in Nisonhoff et al., Arch Biochem. Biophys. 93: 470 (1961). Hammerling et al., J. Exp. Med. 128: 1461 (1968), and U.S. Pat. No. 4,331,647.

More selective linkage can be achieved by using a heterobifunctional linker such as maleimide-hydroxysuccinimide ester. Reaction of the ester with an antibody or fragment will derivatize amine groups on the antibody or fragment, and the derivative can then be reacted with, e. g., an antibody Fab fragment having free sulfhydryl groups (or, a larger fragment or intact antibody with sulfhydryl groups appended thereto by, e. g., Train's Reagent. Such a linker is less likely to crosslink groups in the same antibody and improves the selectivity of the linkage.

It is advantageous to link the antibodies or fragments at sites remote from the antigen binding sites. This can be accomplished by, e. g., linkage to cleaved interchain sulfydryl groups, as noted above. Another method involves reacting an antibody having an oxidized carbohydrate portion with another antibody which has at least one free amine function. This results in an initial Schiff base (imine) linkage, which is preferably stabilized by reduction to a secondary amine, e. g., by borohydride reduction, to form the final product. Such site-specific linkages are disclosed, for small molecules, in U.S. Pat. No. 4,671,958, and for larger addends in U.S. Pat. No. 4,699,784.

Alternatively, such bispecific antibodies can be produced by fusing two hybridoma cell lines that produce appropriate Mabs. Techniques for producing tetradomas are described, for example, by Milstein et al., *Nature* 305: 537 (1983) and Pohl et al., *Int. J. Cancer* 54: 418 (1993).

Alternatively, chimeric genes can be designed that encode both binding domains. General techniques for producing bispecific antibodies by genetic engineering are described, for example, by Songsivilai et al., *Biochem Biophys Res. Commun* 164: 271 (1989); Traunecker et al., *EMBO J.* 10: 3655 (1991); and Weiner et al., *J. Immunol.* 147: 4035 (1991).

A higher order multivalent, multispecific molecule can be obtained by adding various antibody components to a bispecific antibody, produced as above. For example, a bispecific antibody can be reacted with 2-iminothiolane to introduce one or more sulfhydryl groups for use in coupling the bispecific antibody to a further antibody derivative that binds an the same or a different epitope of the target antigen, using the bis-maleimide activation procedure described above. These techniques for producing multivalent antibodies are well known to those of skill in the art. See, for example, U.S. Pat. No. 4,925,648, and Goldenberg, international publication No. WO 92/19273, which are incorporated by reference.

DOCK-AND-LOCK® (DNL®)

In preferred embodiments, a bispecific or multispecific antibody is formed as a DOCK-AND-LOCK® (DNL®) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264. Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL® complex comprises a trimer with two DDD-linked molecules attached to one AD-linked molecule, variations in complex structure allow the formation of dimers, trimers, tetramers, pentamers, hexamers and other multimers. In some embodiments, the DNL® complex may comprise two or more antibodies, antibody fragments or fusion proteins which bind to the same antigenic determinant or to two or more different antigens. The DNL® complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., *J. Biol. Chem.* 1968; 243:3763). The structure of the holoenzyme consists of two catalytic subunits held in an inactive form by the R subunits (Taylor, *J. Biol. Chem.* 1989; 264:8443). Isozymes of PKA are found with two types of R subunits (RI and RII), and each type has α and β isoforms (Scott, *Pharmacol. Ther.* 1991; 50:123). Thus, the four isoforms of PKA regulatory subunits are RIIα, RIIβ, RIIα and RIIβ. The R subunits have been isolated only as stable dimers and the dimerization domain has been shown to consist of the first 44 amino-terminal residues of RIIα (Newlon et al., *Nat. Struct. Biol.* 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci USA.* 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell Biol.* 2004; 5:959). The AD of AKAPs for PKA is an amphipathic helix of 14-18 residues (Carr et al., *J. Biol. Chem.* 1991; 266:14188). The amino acid sequences of the AD are quite varied among individual AKAPs, with the binding affinities reported for RII dimers ranging from 2 to 90 nM (Alto et al., *Proc. Natl. Acad. Sci. USA.* 2003; 100:4445). AKAPs will only bind to dimeric R subunits. For human RIIα, the AD binds to a hydrophobic surface formed by the 23 amino-terminal residues (Colledge and Scott, *Trends Cell Biol.* 1999; 6:216). Thus, the dimerization domain and AKAP binding domain of human RIIα are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL® complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL® constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL® construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL® constructs, different AD or DDD sequences may be utilized. Exemplary DDD and AD sequences are provided below.

```
DDD1
                                    (SEQ ID NO: 1)
SHIQIPPGLTELLQGYTVEVLRQQPPDLVEFAVEYFTRLREARA

DDD2
                                    (SEQ ID NO: 2)
CGHIQIPPGLTELLQGYTVEVLRQQPPDLVEFAVEYFTRLREARA

AD1
                                    (SEQ ID NO: 3)
QIEYLAKQIVDNAIQQA

AD2
                                    (SEQ ID NO: 4)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                    (SEQ ID NO: 5)
SLRECELYVQKHNIQALLKDSIVQLCTARPERPMAFLREYFERLEKEEAK

DDD3C
                                    (SEQ ID NO: 6)
MSCGGSLRECELYVQKHNIQALLKDSIVQLCTARPERPMAFLREYFERLE
KEEAK

AD3
                                    (SEQ ID NO: 7)
CGFEELAWKIAKMIWSDVFQQGC
```

In other alternative embodiments, other sequence variants of AD and/or DDD moieties may be utilized in construction of the DNL® complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                    (SEQ ID NO: 8)
SLRECELYVQKHNIQALLKDVSIVQLCTARPERPMAFLREYFEKLEKEEA
K

PKA RIβ
                                    (SEQ ID NO: 9)
SLKGCELYVQLHGIQQVLKDCIVHLCISKPERPMKFLREHFEKLEKEENR
QILA

PKA RIIα
                                    (SEQ ID NO: 10)
SHIQIPPGLTELLQGYTVEVGQQPPDLVDFAVEYFTRLREARRQ

PKA RIIβ
                                    (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                    (SEQ ID NO: 1)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 1. In devising Table 1, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, *Proc Natl Acad Sci USA* 100:4445-50).

(SEQ ID NO: 23)
SHIQIPPGLTELLQGYTVEVLKQQPPDLVEFAVEYFTRLREARA (SEQ ID NO: 24)
SHIQIPPGLTELLQGYTVEVLRNQPPDLVEFAVEYFTRLREARA (SEQ ID NO: 25)
SHIQIPPGLTELLQGYTVEVLRQNPPDLVEFAVEYFTRLREARA (SEQ ID NO: 26)
SHIQIPPGLTELLQGYTVEVLRQQPPELVEFAVEYFTRLREARA (SEQ ID NO: 27)
SHIQIPPGLTELLQGYTVEVLRQQPPDLVDFAVEYFTRLREARA (SEQ ID NO: 28)
SHIQIPPGLTELLQGYTVEVLRQQPPDLVEFLVEYFTRLREARA (SEQ ID NO: 29)
SHIQIPPGLTELLQGYTVEVLRQQPPDLVEFIVEYFTRLREARA (SEQ ID NO: 30)
SHIQIPPGLTELLQGYTVEVLRQQPPDLVEFVVEYFTRLREARA (SEQ ID NO: 31)
SHIQIPPGLTELLQGYTVEVLRQQPPDLVEFAVDYFTRLREARA

TABLE 1

Conservative Amino Acid Substitutions in DDD1 (SEQ ID NO: 1). Consensus sequence disclosed as SEQ ID NO: 87.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K | N | N |   |   |   | A | S | D |   |   |   | N | A | S |   | D |   | V |   | K |
|   | R |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E | L |   | D | D | D | L | D | S |   |   | K | L | K | D | L | K | L |
|   |   |   |   |   | I |   |   |   |   | I |   |   |   |   |   | I |   |   |   |   | I |
|   |   |   |   |   | V |   |   |   |   | V |   |   |   |   |   | V |   |   |   |   | V |

(SEQ ID NO: 12)
THIQIPPGLTELLQGYTVEVLRQQPPDLVEFAVEYFTRLREARA (SEQ ID NO: 13)
SKIQIPPGLTELLQGYTVEVLRQQPPDLVEFAVEYFTRLREARA (SEQ ID NO: 14)
SRIQIPPGLTELLQGYTVEVLRQQPPDLVEFAVEYFTRLREARA (SEQ ID NO: 15)
SHINIPPGLTELLQGYTVEVLRQQPPDLVEFAVEYFTRLREARA (SEQ ID NO: 16)
SHIQIPPALTELLQGYTVEVLRQQPPDLVEFAVEYFTRLREARA (SEQ ID NO: 17)
SHIQIPPGLSELLQGYTVEVLRQQPPDLVEFAVEYFTRLREARA (SEQ ID NO: 18)
SHIQIPPGLTDLLQGYTVEVLRQQPPDLVEFAVEYFTRLREARA (SEQ ID NO: 19)
SHIQIPPGLTELLNGYTVEVLRQQPPDLVEFAVEYFTRLREARA (SEQ ID NO: 20)
SHIQIPPGLTELLQAYTVEVLRQQPPDLVEFAVEYFTRLREARA (SEQ ID NO: 21)
SHIQIPPGLTELLQGYSVEVLRQQPPDLVEFAVEYFTRLREARA (SEQ ID NO: 22)
SHIQIPPGLTELLQGYTVDVLRQQPPDLVEFAVEYFTRLREARA

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 2 shows potential conservative amino acid substitutions in the sequence of AKAP-IS (AD1, SEQ ID NO:3), similar to that shown for DDD1 (SEQ ID NO:1) in Table 1 above.

A limited number of such potential alternative AD moiety sequences are shown in SEQ ID NO:32 to SEQ ID NO:49 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

AKAP-IS
QIEYLAKQIVDNAIQQA            (SEQ ID NO: 3)

TABLE 2

Conservative Amino Acid Substitutions in AD1 (SEQ ID NO: 3).
Consensus sequence disclosed as SEQ ID NO: 88.

| Q | I | E | Y | L | A | K | Q | I | V | D | N | A | I | Q | Q | A |
|---|---|---|---|---|---|---|---|---|---|---|---|---|---|---|---|---|
| N | L | D | F | I |   | R | N |   |   | E | Q |   |   | N | N | L |
|   | V |   | T | V |   |   |   |   |   |   |   |   |   |   |   | I |
|   |   |   | S |   |   |   |   |   |   |   |   |   |   |   |   | V |

| | |
|---|---|
| NIEYLAKQIVDNAIQQA | (SEQ ID NO: 32) |
| QLEYLAKQIVDNAIQQA | (SEQ ID NO: 33) |
| QVEYLAKQIVDNAIQQA | (SEQ ID NO: 34) |
| QIDYLAKQIVDNAIQQA | (SEQ ID NO: 35) |
| QIEFLAKQIVDNAIQQA | (SEQ ID NO: 36) |
| QIETLAKQIVDNAIQQA | (SEQ ID NO: 37) |
| QIESLAKQIVDNAIQQA | (SEQ ID NO: 38) |
| QIEYIAKQIVDNAIQQA | (SEQ ID NO: 39) |
| QIEYVAKQIVDNAIQQA | (SEQ ID NO: 40) |
| QIEYLARQIVDNAIQQA | (SEQ ID NO: 41) |
| QIEYLAKNIVDNAIQQA | (SEQ ID NO: 42) |
| QIEYLAKQIVENAIQQA | (SEQ ID NO: 43) |
| QIEYLAKQIVDQAIQQA | (SEQ ID NO: 44) |
| QIEYLAKQIVDNAINQA | (SEQ ID NO: 45) |
| QIEYLAKQIVDNAIQNA | (SEQ ID NO: 46) |
| QIEYLAKQIVDNAIQQL | (SEQ ID NO: 47) |
| QIEYLAKQIVDNAIQQI | (SEQ ID NO: 48) |
| QIEYLAKQIVDNAIQQV | (SEQ ID NO: 49) |

Gold et al. (2006, Mol Cell 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL® constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

| | |
|---|---|
| SuperAKAP-IS | |
| QIEYVAKQIVDYAIHQA | (SEQ ID NO: 50) |

Alternative AKAP sequences
| | |
|---|---|
| QIEYKAKQIVDHAIHQA | (SEQ ID NO: 51) |
| QIEYHAKQIVDHAIHQA | (SEQ ID NO: 52) |
| QIEYVAKQIVDHAIHQA | (SEQ ID NO: 53) |

FIG. 2 of Gold et al. disclosed additional DDD-binding sequences from a variety of AKAP proteins, shown below.

RII-Specific AKAPs

| | |
|---|---|
| AKAP-KL | |
| PLEYQAGLLVQNAIQQAI | (SEQ ID NO: 54) |
| AKAP79 | |
| LLIETASSLVKNAIQLSI | (SEQ ID NO: 55) |
| AKAP-Lbc | |
| LIEEAASRIVDAVIEQVK | (SEQ ID NO: 56) |

RI-Specific AKAPs

| | |
|---|---|
| AKAPce | |
| ALYQFADRFSELVISEAL | (SEQ ID NO: 57) |
| RIAD | |
| LEQVANQLADQIIKEAT | (SEQ ID NO: 58) |
| PV38 | |
| FEELAWKIAKMIWSDVF | (SEQ ID NO: 59) |

Dual-Specificity AKAPs

| | |
|---|---|
| AKAP7 | |
| ELVRLSKRLVENAVLKAV | (SEQ ID NO: 60) |
| MAP2D | |
| TAEEVSARIVQVVTAEAV | (SEQ ID NO: 61) |
| DAKAP1 | |
| QIKQAAFQLISQVILEAT | (SEQ ID NO: 62) |
| DAKAP2 | |
| LAWKIAKMIVSDVMQQ | (SEQ ID NO: 63) |

Stokka et al. (2006, Biochem J 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

| | |
|---|---|
| Ht31 | |
| DLIEEAASRIVDAVIEQVKAAGAY | (SEQ ID NO: 64) |
| RIAD | |
| LEQYANQLADQIIKEATE | (SEQ ID NO: 65) |
| PV-38 | |
| FEELAWKIAKMIWSDVFQQC | (SEQ ID NO: 66) |

Hundsrucker et al. (2006, *Biochem J* 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

AKAP Peptide sequences

|  | Peptide Sequence |
|---|---|
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

AKAP-IS
QIEYL<u>AKQI</u>VDN<u>AIQQA</u>     (SEQ ID NO: 3)

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SH<u>IQ*IPP*GLTELLQGYTVEVLRQQPPDLVEFAVEYFTRLREA*R*A</u>

A modified set of conservative amino acid substitutions for the DDD1 (SEQ ID NO:1) sequence, based on the data of Carr et al. (2001) is shown in Table 4. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 1 and Table 2.

TABLE 4

Conservative Amino Acid Substitutions in DDD1 (SEQ ID NO: 1). Consensus sequence disclosed as SEQ ID NO: 89.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   | S |   |   |   |   |   |   |   |   |   | I |   |   |   |
|   |   |   |   |   |   |   |   |   |   |   |   |   |   |   |   |   |   | L |   |   |   |
|   |   |   |   |   |   |   |   |   |   |   |   |   |   |   |   |   |   | A |   |   |   |

TABLE 4-continued

Conservative Amino Acid Substitutions in DDD1 (SEQ ID NO: 1). Consensus sequence disclosed as SEQ ID NO: 89.

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   |   |   |   |   | L | D |   |   | S | K |   | K |   | L |   | L |
|   |   |   |   |   |   |   |   |   |   | I |   |   |   |   |   |   |   |   | I |   | I |
|   |   |   |   |   |   |   |   |   |   | V |   |   |   |   |   |   |   |   | V |   | V |

The skilled artisan will realize that these and other amino acid substitutions in the DDD or AD amino acid sequences may be utilized to produce alternative species within the genus of AD or DDD moieties, using techniques that are standard in the field and only routine experimentation.

Alternative DNL® Structures

In certain alternative embodiments, DNL® constructs may be formed using alternatively constructed antibodies or antibody fragments, in which an AD moiety may be attached at the C-terminal end of the kappa light chain ($C_k$), instead of the C-terminal end of the Fc on the heavy chain. The alternatively formed DNL® constructs may be prepared as disclosed in Provisional U.S. Patent Application Ser. Nos. 61/654,310, filed Jun. 1, 2012, 61/662,086, filed Jun. 20, 2012, 61/673,553, filed Jul. 19, 2012, and 61/682,531, filed Aug. 13, 2012, the entire text of each incorporated herein by reference. The light chain conjugated DNL® constructs exhibit enhanced Fc-effector function activity in vitro and improved pharmacokinetics, stability and anti-lymphoma activity in vivo (Rossi et al., 2013, Bioconjug Chem 24:63-71).

$C_k$-conjugated DNL® constructs may be prepared as disclosed in Provisional U.S. Patent Application Ser. Nos. 61/654,310, 61/662,086, 61/673,553, and 61/682,531. Briefly, $C_k$-AD2-IgG, was generated by recombinant engineering, whereby the AD2 peptide was fused to the C-terminal end of the kappa light chain. Because the natural C-terminus of $C_K$ is a cysteine residue, which forms a disulfide bridge to $C_H1$, a 16-amino acid residue "hinge" linker was used to space the AD2 from the $C_K$-$V_H1$ disulfide bridge. The mammalian expression vectors for $C_k$-AD2-IgG-veltuzumab and $C_k$-AD2-IgG-epratuzumab were constructed using the pdHL2 vector, which was used previously for expression of the homologous $C_H3$-AD2-IgG modules. A 2208-bp nucleotide sequence was synthesized comprising the pdHL2 vector sequence ranging from the Bam HI restriction site within the $V_K/C_K$ intron to the Xho I restriction site 3' of the $C_k$ intron, with the insertion of the coding sequence for the hinge linker (EFPKPSTPPGSSGGAP, SEQ ID NO:126) and AD2, in frame at the 3'end of the coding sequence for $C_K$. This synthetic sequence was inserted into the IgG-pdHL2 expression vectors for veltuzumab and epratuzumab via Bam HI and Xho I restriction sites. Generation of production clones with SpESFX-10 were performed as described for the $C_H3$-AD2-IgG modules. $C_k$-AD2-IgG-veltuzumab and $C_k$-AD2-IgG-epratuzumab were produced by stably-transfected production clones in batch roller bottle culture, and purified from the supernatant fluid in a single step using Mab Select (GE Healthcare) Protein A affinity chromatography.

Following the same DNL® process described previously for 22-(20)-(20) (Rossi et al., 2009, Blood 113:6161-71), $C_k$-AD2-IgG-epratuzumab was conjugated with $C_H1$-DDD2-Fab-veltuzumab, to generate the bsHexAb 22*-(20)-(20), where the 22* indicates the $C_k$-AD2 module of epratuzumab and each (20) symbolizes a stabilized dimer of veltuzumab Fab. The properties of 22*-(20)-(20) were compared with those of 22-(20)-(20), the homologous Fc-bsHexAb comprising $C_H3$-AD2-IgG-epratuzumab, which has similar composition and molecular size, but a different architecture.

Following the same DNL® process described previously for 20-2b (Rossi et al., 2009, Blood 114:3864-71), $C_k$-AD2-IgG-veltuzumab, was conjugated with IFNα2b-DDD2, a module of IFNα2b with a DDD2 peptide fused at its C-terminal end, to generate 20*-2b, which comprises veltuzumab with a dimeric IFNα2b fused to each light chain. The properties of 20*-2b were compared with those of 20-2b, which is the homologous Fc-IgG-IFNα.

Each of the bsHexAbs and IgG-IFNα were isolated from the DNL® reaction mixture by MabSelect affinity chromatography. The two $C_k$-derived prototypes, an anti-CD22/CD20 bispecific hexavalent antibody, comprising epratuzumab (anti-CD22) and four Fabs of veltuzumab (anti-CD20), and a CD20-targeting immunocytokine, comprising veltuzumab and four molecules of interferon-α2b, displayed enhanced Fc-effector functions in vitro, as well as improved pharmacokinetics, stability and anti-lymphoma activity in vivo, compared to their Fc-derived counterparts.

Amino Acid Substitutions

In alternative embodiments, the disclosed methods and compositions may involve production and use of proteins or peptides with one or more substituted amino acid residues. For example, the DDD and/or AD sequences used to make DNL® constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry*, 13:222-245; 1978, *Ann. Rev. Biochem.*, 47: 251-276; 1979, *Biophys. J.*, 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S) thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:85) and veltuzumab (SEQ ID NO:86).

```
Rituximab heavy chain variable region sequence
                                        (SEQ ID NO: 85)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Veltuzumab heavy chain variable region
                                        (SEQ ID NO: 86)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLEPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Jefferis and Lefranc (2009, *mAbs* 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzamab

| | | Heavy chain position and associated allotypes | | | | | |
|---|---|---|---|---|---|---|---|
| | Complete allotype | 214 (allotype) | | 356/358 (allotype) | | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Exemplary antibody constant region sequences of use in the chimeric and humanized anti-histone antibodies are disclosed in SEQ ID NO:127 and SEQ ID NO:128 below.

```
Exemplary human heavy chain constant region
                                    (SEQ ID NO: 127)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

Exemplary human light chain constant region
                                    (SEQ ID NO: 128)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC
```

Immunoconjugates

In certain embodiments, the antibodies or fragments thereof may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSSLINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F—Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used, either conjugated to the subject anti-histone antibodies or separately administered before, simultaneously with, or after the anti-histone antibody. Drugs of use may possess a pharmaceutical property selected from the group consisting of antimitotic, antikinase (e.g., anti-tyrosine kinase), alkylating, antimetabolite, antibiotic, alkaloid, anti-angiogenic, pro-apoptotic agents, immune modulators, and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-ß, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -ß; mullerian-inhibiting substance; mouse gonadotropin-associated peptide; inhibin; activin; vascular endothelial growth factor; integrin; thrombopoietin (TPO); nerve growth factors such as NGF-ß; platelet-growth factor; transforming growth factors (TGFs) such as TGF-α and TGF-ß; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. Lenolidamide is yet another immunomodulator that has shown activity in controlling certain cancers, such as multiple myeloma and hematopoietic tumors.

Radionuclides of use include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{211}$Pb and $^{227}$Th. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227, and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$Cu, $^{67}$Ga, $^{67}$Ga, $^{68}$Ga, $^{86}$Y, $^{89}$Zr, $^{94}$Tc, $^{94m}$Tc, $^{99m}$Tc, or, $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, *Chem. Britain* (1986), 22:430. Moreover, monoclonal antibodies have been coupled with photoactivated dyes for achieving phototherapy. See Mew et al., *J. Immunol.* (1983), 130:1473; idem., *Cancer Res.* (1985), 45:4380; Oseroff et al., *Proc. Natl. Acad. Sci. USA* (1986), 83:8744; idem., *Photochem. Photobiol.* (1987), 46:83; Hasan et al., *Prog. Clin. Biol. Res.* (1989), 288:471; Tatsuta et al., *Lasers Surg. Med.* (1989), 9:422; Pelegrin et al., *Cancer* (1991), 67:2529.

Other useful therapeutic agents may comprise oligonucleotides, especially antisense oligonucleotides that preferably are directed against oncogenes and oncogene products, such as bcl-2. A preferred form of therapeutic oligonucleotide is siRNA.

Diagnostic Agents

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Immune Dysregulatory Disease, Infectious Disease and Inflammatory Disease

In various embodiments, the anti-histone antibodies or fragments thereof are of use to treat inflammatory or immune-dysregulatory diseases, such as sepsis, septic shock, septicemia, acute respiratory distress syndrome, graft-vs. host disease (GVHD), transplant rejection, atherosclerosis, asthma, granulomatous disease, a neuropathy, cachexia, a coagulopathy, acne, giant cell arteritis or myocardial ischemia, as well as typical autoimmune disease (as listed previously). In certain preferred embodiments, the therapy may utilize either a combination of two or more separate antibodies or fragments thereof, administered together or separately, or else a bispecific or multispecific antibody or antibody fragment, with a first binding site for a histone and a second binding site for a different target antigen. More preferably, a target antigen may be selected from the group consisting of histone H3, histone H4, histone H2B, a proinflammatory effector of the innate immune system, a component or cell of the adaptive immune system, a proinflammatory effector cytokine or chemokine, or a target specifically associated with infectious disease, acute respiratory distress syndrome, septicemia, septic shock, GVHD, transplant rejection, atherosclerosis, asthma, granulomatous disease, a neuropathy, cachexia, a coagulopathy, acne, giant cell arteritis or myocardial ischemia. In some cases, CD74 may be specifically excluded as a potential target antigen, except when the anti-CD74 antibody or inhibitor is combined with an anti-histone antibody. Specific target antigens of use may include, but are not limited to, TNF-α, MIF, CD74, HLA-DR, IL-1, IL-3, IL-4, IL-5, IL-6, IL-8, IL-12, IL-15, IL-17, IL-18, IL-23, IL-4R, IL-6R, IL-13R, IL-15R, IL-17R, IL-18R, CD40L, CD44, CD46, CD55, CD59, CCL19, CCL21, mCRP, MCP-19, MIP-1A, MIP-1B, RANTES, ENA-78, IP-10, GRO-β, lipopolysaccharide, lymphotoxin, HMGB-1, tissue factor, a complement regulatory protein, a coagulation factor, thrombin, a complement factor, C3, C3a, C3b, C4a, C4b, C5, C5a, C5b, Flt-1 and VEGF. Thrombomodulin and/or activated protein C may also be combined with anti-histone antibodies used with any of the above-specified antibodies.

Additional therapeutic agents that may be added in combination include a cytokine, a chemokine, a coagulation inhibitor, an anti-T cell or anti B-cell antibody or antibody fragment, an immunomodulator, a stem cell growth factor, a lymphotoxin, a hematopoietic factor, a colony stimulating factor, an interferon, erythropoietin or thrombopoietin. An optional therapeutic agent may include activated protein C or thrombomodulin, as mentioned above.

Embodiments of the invention relate generally to methods and compositions for immunotherapy of inflammatory and immune-dysregulatory diseases, using multispecific antibodies that target at least two different markers. The markers may be antigens and/or receptors on lymphocytes, macrophages, monocytes, or dendritic cells (DCs). Particular embodiments relate to methods and compositions for modulating receptors on immune-targeting and immune-processing cells using specific antibodies and antibody heteroconjugates to bind to the cells and their receptors, to effect a treatment of various diseases that are generated or exacerbated by, or otherwise involve, these cells and their receptors. Such diseases more particularly include acute and chronic inflammatory disorders, autoimmune diseases, septicemia and septic shock, neuropathies, graft-versus-host disease, acute respiratory distress syndrome, granulomatous diseases, giant cell arteritis, acne, diffuse intravascular coagulation (DIC), transplant rejection, asthma, cachexia, myocardial ischemia, and atherosclerosis. The methods and compositions also are useful in treating pathological angiogenesis and cancer. The methods and compositions can include a secondary therapeutic that is directed to a cancer receptor, a cancer oncogene, or cancer-associated antigen. Methods and compositions are also described for improved diagnosis/detection of the diseases.

Background

The immune system comprises both the innate immune system and the adaptive, or acquired immune system. Many host cells participate in the processes of innate and adaptive immunity, such as neutrophils, T- and B-lymphocytes, macrophages and monocytes, dendritic cells, and plasma cells. They usually act in concert, affecting one another, particularly in the regulation of certain factors and cytokines that contribute to the recognition and processing of innate and external noxients, and these systems have evolved over the millions of years of the development of vertebrate, mammalian, and human organisms.

A major goal of immunotherapy is to exploit or enhance a patient's immune system against an innate or foreign noxient, such as a malignant cell or an invading microorganism. The immune system has been studied more in relation to recognizing and responding to exogenous noxients, such as microbial organisms, than it has in relation to indigenous malfunctions, such as cancer and certain auto-immune and immune-dysregulatory diseases, particularly since the latter may have both genetic as well as environmental components. The defenses against microbial organisms, such as bacteria, fungi, parasites, and viruses, are innate to the particular organism, with the immune system being programmed to recognize biochemical patterns of these microorganisms and to respond to attack them without requiring prior exposure to the microorganism. This innate immune system includes, for example, neutrophils, natural killer cells and monocytes/macrophages that can eradicate the invading microorganisms by direct engulfment and destruction.

The innate immune response is often referred to as a nonspecific one that controls an invading external noxient until the more specific adaptive immune system can marshal specific antibodies and T cells (cf. Modlin et al., N Engl J Med 1999, 340:1834-1835; Das, Crit. Care 2000; 4:290-296). The nonspecific immune responses involve the lymphatic system and phagocytes. The lymphatic system includes the lymphocytes and macrophages. Macrophages can engulf, kill and dispose of foreign particles. Phagocytes include neutrophils and macrophages, which again ingest, degrade and dispose of debris, and have receptors for complement and antibody. In summary, the innate immune system provides a line of defense again certain antigens because of inherited characteristics.

In contrast, the adaptive, or acquired, immune system, is highly evolved and very specific in its responses. It is called an adaptive system because is occurs during the lifetime of an individual as an adaptation to infection with a pathogen. Adaptive immunity can be artificially acquired in response to a vaccine (antigens) or by administering antibodies, or can be naturally acquired by infection. The acquired immunity can be active, if an antibody was produced, or it can be passive, if exogenous antibody made form another source is injected.

The adaptive immune system produces antibodies specific to a given antigen. The simplest and most direct way in which antibodies provide protection is by binding to them and thereby blocking their access to cells that they may infect or destroy. This is known as neutralization. Binding by antibodies, however, is not sufficient to arrest the replication of bacteria that multiply outside cells. In this case, one role of antibody is to enable a phagocytic cell to ingest and destroy the bacterium. This is known as opsonization. The third function of antibodies is to activate a system of plasma proteins, known as complement. In many cases, the adaptive immune system confers lifelong protective immunity to re-infection with the same pathogen, because the adaptive immune system has a 'memory' of the antigens presented to it.

Antibody-mediated immunity is called humoral immunity and is regulated by B cells and the antibodies they produce. Cell-mediated immunity is controlled by T cells. Both humoral and cell-mediated immunity participate in protecting the host from invading organisms. This interplay can result in an effective killing or control of foreign organisms. Occasionally, however, the interplay can become erratic. In these cases, there is a dysregulation that can cause disease. Sometimes the disease is life-threatening, such as with septic shock and certain autoimmune disorders.

The B and T lymphocytes are critical components of a specific immune response. B cells are activated by antigen to engender clones of antigen-specific cells that mediate adaptive immunity. Most clones differentiate to plasma cells that secrete antibody, while a few clones form memory cells that revert to plasma cells. Upon subsequent re-infection, memory cells produce a higher level of antibody in a shorter period than in the primary response. Antibodies secreted by the plasma cells can play multiple roles in immunity, such as binding and neutralizing a foreign agent, acting as opsonins (IgG) to promote phagocytosis, directly affecting metabolism and growth of some organisms, engaging in antigen-antibody reactions that activate complement, causing phagocytosis and membrane attack complex, and/or engaging in antigen-antibody reactions that activate T cells and other killer cells.

T lymphocytes function as both helper cells and suppressor cells. Helper T cells induce antigen-specific B cells and effector T cells to proliferate and differentiate. Suppressor T cells interact with helper T cells to prevent an immune response or to suppress an ongoing one, or to regulate effector T cells. Cytotoxic T cells destroy antigen by binding to target cells. In a delayed-type hypersensitivity reaction, the T cells do not destroy antigen, but attract macrophages, neutrophils and other cells to destroy and dispose of the antigen.

T cells can detect the presence of intracellular pathogens because infected cells display on their surface peptide fragments derived from the pathogens' proteins. These foreign peptides are delivered to the cell surface by specialized host-cell glycoproteins, termed Major Histocompatibility Complex (MHC) molecules. The recognition of antigen as a small peptide fragment bound to a MHC molecule and displayed at the cell surface is one of the most distinctive features of T cells. There are two different classes of MHC molecules, know as MHC class I and MHC class II, that deliver peptides from different cellular compartments to the surface of the infected cell. Peptides from the cytosol are bound to MHC class I molecules which are expressed on the majority of nucleated cells and are recognized by CD8+ T cells. MHC class II molecules, in contrast, traffic to lysosomes for sampling endocytosed protein antigens which are presented to the CD4+ T cells (Bryant and Ploegh, *Curr Opin Immunol* 2004; 16:96-102).

CD8+ T cells differentiate into cytotoxic T cells, and kill the cell. CD4+ T cells differentiate into two types of effector T cells. Pathogens that accumulate in large numbers inside macrophage vesicles tend to stimulate the differentiation of $T_{H1}$ cells which activate macrophages and induce B cells to make IgG antibodies that are effective in opsonizing extracellular pathogens for uptake by phagocytes. Extracellular antigens tend to stimulate the production of $T_{H2}$ cells which initiate the humoral immune response by activating naive antigen-specific B cells to produce IgM antibodies, inter alia.

The innate and adaptive immune systems interact, in that the cells of the innate immune system can express various molecules that can interact with or trigger the adaptive immune system by activating certain cells capable of producing immune factors, such as by activating T and B cells of the lymphatic series of leukocytes. The early induced but non-adaptive responses are important for two main reasons. First, they can repel a pathogen or, more often, control it until an adaptive immune response can be mounted. Second, these early responses influence the adaptive response in several ways. For example, the innate immune response produces cytokines and other inflammatory mediators that have profound effects on subsequent events, including the recruitment of new phagocytic cells to local sites of infection. Another effect of these mediators is to induce the expression of adhesion molecules on the endothelial cells of the local blood vessels, which bind to the surface of circulating monocytes and neutrophils and greatly increase their rate of migration of these cells out of the blood and into the tissues. These events all are included under the term inflammation, which is a feature of the innate immune system that forms part of the protective response at a localized site to isolate, destroy and remove a foreign material. This is followed by repair. Inflammation is divided into acute and chronic forms.

The immune system communicates via nonspecific tissue resistance factors. These include the interferons, which are proteins produced in response to viruses, endotoxins and certain bacteria. Interferons inhibit viral replication and activate certain host-defense responses. Infected cells produce interferon that binds the infected cells to other, neighboring cells, causing them to produce antiviral proteins and enzymes that interfere with viral gene transcription and proteins synthesis. Interferons can also affect normal cell growth and suppress cell-mediated immunity.

Complement is another nonspecific tissue resistance factor, and comprises plasma proteins and membrane proteins that mediate specific and non-specific defenses. Complement has two pathways, the classical pathway associated with specific defense, and the alternative pathway that is activated in the absence of specific antibody, and is thus non-specific. In the classical pathway, antigen-antibody complexes are recognized when C1 interacts with the Fc of the antibody, such as IgM and to some extent, IgG, ultimately causing mast cells to release chemotactic factors, vascular mediators and a respiratory burst in phagocytes, as one of many mechanisms. The key complement factors include C3a and C5a, which cause mast cells to release chemotactic factors such as histamine and serotonin that attract phagocytes, antibodies and complement, etc. Other key complement factors are C3b and C5b, which enhance phagocytosis of foreign cells, and C8 and C9, which induce lysis of foreign cells (membrane attack complex).

Cancer cells can escape immune surveillance by avoiding complement activation, especially by the expression of membrane-associated complement regulatory proteins, such as CD55 (decay-accelerating factor), CD46 (membrane cofactor protein), and CD59 (protectin), and it is believed that the over-expression of these proteins on cancer cell membranes protects these cancers from complement activation (Brasoveanu et al., *Lab Invest* 1996; 74:33-42; Jarvis et al., *Int J Cancer* 1997; 71:1049-1055; Yu et al., *Clin Exp Immunol* 1999; 115:13-18; Murray et al., *Gynecol Oncol* 2000; 76:176-182; Donin et al., *Clin Exp Immunol* 2003; 131:254-263). Attempts have been made, unsuccessfully, to increase the susceptibility to complement-mediated lysis by use of neutralizing antibodies against CD46, CD55 and CD59 (Varsano et al., *Clin Exp Immunol* 1998; 113:173-182 Junnikkala et al., *J Immunol* 2000; 164:6075-6081; Maenpaa et al., *Am J Pathol* 1996; 148:1139-1162; Goiter, *Lab Invest* 1996; 74:1039-1049. In the latter study, CD46 and CD55 antibodies were, in contrast to CD59 antibodies, ineffective. This suggests that other targets, or the use of antibodies against multiple complement regulatory proteins, or against both complement regulatory proteins and other mediators of immunity may be required. This general failure contradicts the speculation of Fishelson et al. (*Mol Immunol* 2003: 40:109-123) and the suggestion from other studies that treatment of cancer patients with antibodies to membrane complement regulatory proteins in combination with anti-cancer complement-fixing antibodies will improve therapeutic efficacy.

Gelderman et al. (*Mol Immunol* 2003; 40:13-23) reported that membrane-bound complement regulatory proteins (mCRP) inhibit complement activation by an immunotherapeutic mAb in a syngeneic rat colorectal cancer model. While the use of mAb against tumor antigens and mCRP overcame an observed effect of mCRP on tumor cells, there has been no direct evidence to support this approach. Still other attempts to use bispecific antibodies against CD55 and against a tumor antigen (G250 or EpCAM) have been suggested by Gelderman et al. (*Lab Invest* 2002; 82:483-493; *Eur J Immunol* 2002; 32:128-135) based on in vitro studies that showed a 2-13-fold increase in C3 deposition compared to use of the parental antitumor antibody. However, no results involving enhanced cell killing were reported. Jurianz et al. (*Immunopharmacology* 1999; 42:209-218) also suggested that combining treatment of a tumor with anti-HER2 antibodies in vitro could be enhanced by prior treatment with antibody-neutralization of membrane-complement-regulatory protein, but again no in vivo results were provided. Sier et al. (*Int J Cancer* 2004; 109:900-908) recently reported that a bispecific antibody made against an antigen expressed on renal cell carcinoma (Mab G250) and CD55 enhanced killing of renal cancer cells in spheroids when beta-glucan was added, suggesting that the presence of CR3-priming beta-glucan was obligatory.

Neutrophils, another cell involved in innate immune response, also ingest, degrade and dispose of debris. Neutrophils have receptors for complement and antibody. By means of complement-receptor bridges and antibody, the foreign noxients can be captured and presented to phagocytes for engulfment and killing.

Macrophages are white blood cells that are part of the innate system that continually search for foreign antigenic substances. As part of the innate immune response, macrophages engulf, kill and dispose of foreign particles. However, they also process antigens for presentation to B and T cells, invoking humoral or cell-mediated immune responses.

The dendritic cell is one of the major means by which innate and adaptive immune systems communicate (Reis e Sousa, *Curr Opin Immunol* 2004; 16:21-25). It is believed that these cells shape the adaptive immune response by the reactions to microbial molecules or signals. Dendritic cells capture, process and present antigens, thus activating CD4+ and CD8+ naive T lymphocytes, leading to the induction of primary immune responses, and derive their stimulatory potency from expression of MHC class I, MHC class II, and accessory molecules, such as CD40, CD54, CD80, CD86, and T-cell activating cytokines (Steinman, *J Exp Hematol* 1996; 24:859-862; Banchereau and Steinman, *Nature* 1998; 392:245-252). These properties have made dendritic cells candidates for immunotherapy of cancers and infectious diseases (Nestle, *Oncogene* 2000; 19:673-679; Fong and Engleman, *Annu Rev Immunol* 2000; 18:245-273; Lindquist and Pisa, *Med Oncol* 2002; 19:197-211), and have been shown to induce antigen-specific cytotoxic T cells that result in strong immunity to viruses and tumors (Kono et al., Clin *Cancer Res* 2002; 8:394-40).

Also important for interaction of the innate and adaptive immune systems is the NK cell, which appears as a lymphocyte but behaves like a part of the innate immune system. NK cells have been implicated in the killing of tumor cells as well as essential in the response to viral infections (Lanier, *Curr Opin Immunol* 2003; 15:308-314; Carayannopoulos and Yokoyama, *Curr Opin Immunol* 2004; 16:26-33). Yet another important mechanism of the innate immune system is the activation of cytokine mediators that alert other cells of the mammalian host to the presence of infection, of which a key component is the transcription factor NF-κB (Li and Verna, *Nat Rev Immunol* 2002; 2:725-734).

As mentioned earlier, the immune system can overreact, resulting in allergies or autoimmune diseases. It can also be suppressed, absent, or destroyed, resulting in disease and death. When the immune system cannot distinguish between "self" and "nonself," it can attach and destroy cells and tissues of the body, producing autoimmune diseases, e.g., juvenile diabetes, multiple sclerosis, myasthenia gravis, systemic lupus erythematosus, rheumatoid arthritis, and immune thrombocytopenic purpura. Immunodeficiency disease results from the lack or failure of one or more parts of the immune system, and makes the individuals susceptible to diseases that usually do not affect individuals with a normal immune system. Examples of immunodeficiency disease are severe combined immunodeficiency disease (SCID) and acquired immunodeficiency disease (AIDS). The latter results from human immunodeficiency virus (HIV) and the former from enzyme or other inherited defects, such as adenosine deaminase deficiency.

The application of immunotherapy to cancer involves a number of approaches to engage or exploit the immune system, such as adoptive transfer of anti-tumor-reactive T cells and the use of vaccines, as well as breaking tolerance to tumor self-antigens by inhibiting regulatory cells, and boosting T-cell immunity by use of various cytokines and so-called immune-enhancing molecules (Antonia et al., *Curr Opin Immunol* 2004; 16:130-136). Dendritic-cell vaccines have also been described. Direct and indirect (mediated by host effector cells) actions of antibodies administered to patients by targeting tumor-cell antigens/receptors have now entered the cancer therapy armamentarium, as exemplified by antibodies against CD20 and CD52 in the therapy of lymphomas and leukemia; anti-epidermal growth factor receptor (EGFR), the anti-HER2/neu variant, in the therapy of diverse solid tumors; and anti-vascular endothelium growth factor (VEGF) for the treatment of certain solid tumors. Although active when given alone, most of these show enhanced antitumor effects when combined with other treatment modalities, such as drugs and radiation. Using these tumor-targeting antibodies to deliver cytotoxic drugs or isotopes is still another method of immunotherapy that has entered the clinic. These and other methods of cancer immunotherapy have been reviewed in Huber and Wolfel, *J Cancer Res Clin Oncol* 2004; 130:367-374. However, at best these approaches show reduction of tumor and improved survival in a proportion of the patients, most of whom eventually relapse, thus requiring other therapeutic interventions and different strategies to control their disease.

Sepsis is a major medical and economic burden to our society, affecting about 700,000 people annually in the United States, causing over 200,000 deaths annually, and costing approximately $16.7 billion per year (Angus et al., *Crit Care Med* 2001; 29:1303-1310; Martin et al., *N Engl J Med* 2003; 348:1546-1554). The definition of sepsis has been difficult, and historically it was defined as the systemic host response to an infection. A discussion of the clinical definition of sepsis, encompassing systemic inflammatory response syndrome (SIRS), sepsis per se, severe sepsis, septic shock, and multiple organ dysfunction syndrome (MODS) is contained in Riedmann et al., *J Clin Invest* 2003; 112:460-467. Since it has been a common belief that sepsis is caused by the host's overwhelming reaction to the invading microorganisms, and that the patient is more endangered by this response that than the invading microorganisms, suppression of the immune and inflammatory responses was an early goal of therapy.

Numerous and diverse methods of immunosuppression or of neutralizing proinflammatory cytokines have proven to be unsuccessful clinically in patients with sepsis and septic shock anti-inflammatory strategies. (Riedmann, et al., cited above; Van Amersfoort et al. (*Clin Microbiol Rev* 2003; 16:379-414), such as general immunosuppression, use of nonsteroidal anti-inflammatory drugs, TNF-α antibody (infliximab) or a TNF-R:Fc fusion protein (etanercept), IL-1 (interleukin-1) receptor antagonist, or high doses of corticosteroids. However, a success in the treatment of sepsis in adults was the PROWESS study (Human Activated Protein C Worldwide Evaluation in Severe Sepsis (Bernard et al., *N Engl J Med* 2001; 344:699-709)), showing a lower mortality (24.7%) than in the placebo group (30.8%). This activated protein C (APC) agent probably inhibits both thrombosis and inflammation, whereas fibrinolysis is fostered. Friggeri et al. (2012, *Mol Med* 18:825-33) reported that APC degrades histones H3 and H4, which block uptake and clearance of apoptotic cells by macrophages and thereby contribute to organ system dysfunction and mortality in acute inflammatory states. Van Amersfoort et al. state, in their review (ibid.) that: "Although the blocking or modulation of a number of other targets including complement and coagulation factors, neutrophil adherence, and NO release, are promising in animals, it remains to be determined whether these therapeutic approaches will be effective in humans." This is further emphasized in a review by Abraham, "Why immunomodulatory therapies have not worked in sepsis" (*Intensive Care Med* 1999; 25:556-566). In general, although many rodent models of inflammation and sepsis have shown encouraging results with diverse agents over the past decade or more, most agents translated to the clinic failed to reproduce in humans what was observed in these animal models, so that there remains a need to provide new agents that can control the complex presentations and multiple-organ involvement of various diseases involving sepsis, coagulopathy, and certain neurodegenerative conditions having inflammatory or immune dysregulatory components.

More recent work on immunoglobulins in sepsis or septic shock has been reported. For example, Toussaint and Gerlach (2012, *Curr Infect Dis Rep* 14:522-29) summarized the use of ivIG as an adjunct therapy in sepsis. The metanalysis failed to show any strong correlation between general immunoglobulin therapy and outcome. LaRosa and Opal (2012, *Curr Infect Dis Rep* 14:474-83) reported on new therapeutic agents of potential use in sepsis. Among other agents, anti-TNF antibodies are in current clinical trials for sepsis, while complement antagonists have shown promising results in preclinical models of sepsis. Nalesso et al. (2012, *Curr Infect Dis Rep* 14:462-73) suggested that combination therapies with multiple agents may prove more effective for sepsis treatment. The immunopathogenesis of sepsis has been summarized by Cohen (2002, *Nature* 420:885-91).

The immune system in sepsis is believed to have an early intense proinflammatory response after infection or trauma, leading to organ damage, but it is also believed that the innate immune system often fails to effectively kill invading microorganisms (Riedmann and Ward, *Expert Opin Biol Ther* 2003; 3:339-350). There have been some studies of macrophage migration inhibitory factor (MIF) in connection with sepsis that have shown some promise. For example, blockage of MIF or targeted disruption of the MIF gene significantly improved survival in a model of septic shock in mice (Calandra et al., *Nature Med* 2000; 6:164-170), and several lines of evidence have pointed to MIF as a potential target for therapeutic intervention in septic patients (Riedmann et al., cited above). Bucala et al. (U.S. Pat. No. 6,645,493 B1) have claimed that an anti-MIF antibody can be effective therapeutically for treating a condition or disease caused by cytokine-mediated toxicity, including different forms of sepsis, inflammatory diseases, acute respiratory disease syndrome, granulomatous diseases, chronic infections, transplant rejection, cachexia, asthma, viral infections, parasitic infections, malaria, and bacterial infections, which is incorporated herein in its entirety, including references. The use of anti-LPS (lipopolysaccharide) antibodies alone similarly has had mixed results in the treatment of patients with septic shock (Astiz and Rackow, *Lancet* 1998; 351: 1501-1505; Van Amersfoort et al., *Clin Microbiol Rev* 2003; 16:379-414.

While both LPS and MIF have been pursued as targets in the treatment of sepsis and septic shock, approaches which target LPS or MIF alone by an antibody have not been sufficient to control the diverse manifestations of sepsis, especially in advanced and severe forms. Similarly, use of cytokines, such as IL-1, IL-6 (interleukin-6), IL-8 (interleukin-8), etc., as targets for antibodies for the treatment of sepsis and other cytokine-mediated toxic reactions, has not proven to be sufficient for a meaningful control of this disease. Therefore, in addition to the need to discover additional targets of the cytokine cascade involved in the endogenous response in sepsis, it has now been discovered that bi- and multi-functional antibodies targeting at least one cytokine or causative agent, such as MIF or lipopolysaccharide (LPS), is advantageous, especially when combined with the binding to a host cell (or its receptor) engaged in the inflammatory or immune response, such as T cells, macrophages or dendritic cells. Antibodies against an MHC class II invariant chain target, such as CD74, have been proposed by Bucala et al. (US 2003/0013122 A1), for treating MIF-regulated diseases, and Hansen et al. (US 2004/0115193 A1) proposed at least one CD74 antibody for treating an immune dysregulation disease, an autoimmune disease, organ graft rejection, and graft-versus-host disease. Hansen et al. describe the use of fusion proteins of anti-CD74 with other antibodies reacting with antigens/receptors on host cells such as lymphocytes and macrophages for the treatment of such diseases. However, combinations with targets other than CD74 are not suggested, and the disclosure focuses on a different method of immunotherapy. Similar targets are also useful to treat atherosclerotic plaques (Burger-Kentischer et al., *Circulation* 2002; 105:1561-1566).

In the treatment of infectious, autoimmune, organ transplantation, inflammatory, and graft-versus-host (and other immunoregulatory) diseases, diverse and relatively non-specific cytotoxic agents are used to either kill or eliminate the noxient or microorganism, or to depress the host's immune response to a foreign graft or immunogen, or the host's production of antibodies against "self," etc. However, these usually affect the lymphoid and other parts of the hematopoietic system, giving rise to toxic effects to the bone marrow (hematopoietic) and other normal host cells. Particularly in sepsis, where an immunosuppressed status is encountered, use of immunosuppressive therapies would be counter-indicated, so it is a goal to effect a careful balance between targeting and inhibiting key cells of the adaptive immune system while not depleting those involved with the host maintaining an active immune system.

A need exists for improved, more selective therapy of cancer and diverse immune diseases, including sepsis and septic shock, inflammation, atherosclerosis, cachexia, graft-versus-host, and other immune dysregulatory disorders.

Summary

Various embodiments concern well-tolerated methods which use compositions comprising multispecific antibodies or a combination of separate antibodies in the therapy of various inflammatory and immune-dysregulatory diseases, infectious diseases, pathologic angiogenesis and cancer. The multispecific antibodies or combinations of antibodies are more effective than agents which react specifically with only one target associated with these conditions. The antibodies react with one or more targets selected from the group consisting of (A) histones, (B) proinflammatory effectors of the innate immune system, (C) coagulation factors, (D) complement factors and complement regulatory proteins, and (E) targets specifically associated with an inflammatory or immune-dysregulatory disorder or with a pathologic angiogenesis or cancer, wherein the latter target is not (A), (B), (C) or (D). At least one of the targets is (A), (B), (C) or (D). Targets of the adaptive immune system, such as specific dendritic cells, macrophages, NK cells, T cells, B cells and their specialized populations also may be selected. When the composition comprises a single multispecific antibody, then CD74 may excluded as a target, unless combined with an anti-histone antibody. Furthermore, when the composition comprises a combination of separate antibodies, combinations are excluded where one of the antibodies targets a B-cell antigen and the other antibody targets a T-cell, plasma cell, macrophage or inflammatory cytokine, unless used in combination with an anti-histone antibody. Combinations of separate antibodies are also excluded where one of the antibodies targets CD20 and the other antibody targets C3b or CD40 or CD40L, except where combined with an anti-histone antibody of this invention.

When the composition comprises a combination of separate antibodies, combinations are excluded where one of the antibodies targets CD19, CD20, CD21, CD22, CD23 or CD80 and the other antibody targets a complement factor. More particularly, combinations are excluded where one of the antibodies targets CD19, CD20, CD21, CD22, CD23 or CD80 and the other antibody targets C3b or CD40. However, any of these can be combined with an anti-histone antibody of this invention.

Targets for Therapy of Immune Dysregulatory Disease, Infectious Disease and Inflammatory Disease The proinflammatory effector of the innate immune system may be a proinflammatory effector cytokine, a proinflammatory effector chemokine or a proinflammatory effector receptor. Suitable proinflammatory effector cytokine include MIF, HMGB-1 (high mobility group box protein 1), TNF-α, IL-1, IL-4 (interleukin-4), IL-5 (interleukin-5), IL-6, IL-8, IL-12 (interleukin-12), IL-15 (interleukin-15), IL-17 (interleukin-17), IL-18 (interleukin-18), and IL-23 (interleukin-23). Examples of proinflammatory effector chemokines include CCL19, CCL21, IL-8, MCP-1, RANTES, MIP-1A, MIP-1B, ENA-78, MCP-1, IP-10, GRO-β, and Eotaxin. Proinflammatory effector receptors include IL-4R (interleukin-4 receptor), IL-6R (interleukin-6 receptor), IL-13R (interleukin-13 receptor), IL-15R (interleukin-15 receptor), IL-17R (interleukin-17 receptor) and IL-18R (interleukin-18 receptor).

The multispecific antibody or combination of antibodies also may react specifically with at least one coagulation factor, particularly tissue factor (TF), thrombomodulin, or thrombin. In other embodiments, the multispecific antibody or combination of antibodies reacts specifically with at least one complement factor or complement regulatory protein. In preferred embodiments, the complement factor is selected from the group consisting of C3, C5, C3a, C3b, and C5a. In these embodiments, target combinations preferably do not include those in which the other antibody targets CD19, CD20, CD21, CD22, CD23 or CD80 when the composition comprises a combination of separate antibodies. When the antibody reacts specifically with a complement regulatory protein, the complement regulatory protein preferably is selected from the group consisting of CD46, CD55, CD59 and mCRP.

In one embodiment, the composition comprises two or more antibodies which differ in specificity, each of which reacts specifically with a different proinflammatory effector of the innate immune system. Alternatively, the composition comprises two or more antibodies that differ in specificity, each of which reacts specifically with a different coagulation factor. In another embodiment, the composition comprises two or more antibodies that differ in specificity, each of which reacts specifically with a different complement factor or complement regulatory protein. In yet other embodiments, the two or more antibodies react specifically with at least one proinflammatory effector of the innate immune system and with at least one coagulation factor, or with at least one proinflammatory effector of the innate immune system and with at least one complement factor or complement regulatory protein, or with at least one complement factor or complement regulatory protein and with at least one coagulation factor, respectively. Alternatively, the multispecific antibody may react specifically with more than one proinflammatory effector of the innate immune system, or with more than one coagulation factor, or with more than one complement factor or complement regulatory protein. Preferred are combinations of the above that include an anti-histone antibody of the current invention.

The two or more antibodies may react specifically with more than one epitope of the same proinflammatory effector of the innate immune system or more than one epitope of the same coagulation factor or more than one epitope of the same complement factor or complement regulatory protein or more than one epitope of a histone. In any of these embodiments, the multispecific antibody additionally may react with a target specifically associated with an inflammatory or immune-dysregulatory disorder or with a pathologic angiogenesis or cancer, which target is not an (A), (B), (C) or (D) target as defined above. In other embodiments, the multispecific antibody reacts with a target specifically associated with an inflammatory or immune-dysregulatory disorder or with a pathologic angiogenesis or cancer, and with one or more (A), (B), (C) or (D) targets as defined above. An example of a useful target for pathologic angiogenesis is Flt-1.

The composition alternatively may comprise at least one soluble receptor, or at least an extracellular domain of at least one proinflammatory effector receptor. In one embodiment, the composition comprises at least one soluble receptor or at least an extracellular domain of a proinflammatory effector receptor fused to at least one antibody.

The composition may comprise at least one molecule reactive with a proinflammatory effector receptor. This molecule preferably is a natural antagonist for the proinflammatory effector receptor, or a fragment or mutant of the antagonist that interacts specifically with the receptor. In one embodiment, the natural antagonist is the natural IL-1 receptor antagonist, or a fragment or mutant of this antagonist.

The multispecific antibody additionally may target dendritic cells, granulocytes, monocytes, macrophages, NK-cells, platelets, or endothelial cells. In some embodiments, the multispecific antibody specifically reacts with at least one antigen or receptor of the adaptive immune system. In other embodiments, the multispecific antibody specifically reacts with a cancer cell receptor, a cancer oncogene, or cancer-associated antigen, such as B-cell lineage antigens (CD19, CD20, CD21, CD22, CD23, etc.), VEGFR, EGFR, carcinoembryonic antigen (CEA), placental growth factor (PLGF), tenascin, HER-2/neu, EGP-1, EGP-2, CD25, CD30, CD33, CD38, CD40, CD45, CD52, CD74, CD80, CD138, NCA66, MUC1, MUC2, MUC3, MUC4, MUC5ac, MUC16, IL-6, α-fetoprotein (AFP), A33, CA125, colon-specific antigen-p (CSAp), folate receptor, HLA-DR, human chorionic gonadotropin (HCG), Ia, EL-2, insulin-like growth factor (ILGF) and ILGF receptor, KS-1, Le(y), MAGE, necrosis antigens, PAM-4 mucin, MUC5ac, prostatic acid phosphatase (PAP), Pr1, prostate specific antigen (PSA), PSMA, S100, T101, TAC, TAG72, TRAIL receptors, or carbonic anhydrase IX. Flt-3, which targets proliferating myeloid bone marrow cells, also is a useful in identifying and treating certain cancers. Alternatively, the multispecific antibody may react specifically with a target such as C5a, Factor H, FHL-1, LPS, IFNγ or B7, or with a target such as CD2, CD4, CD14, CD18, CD11a, CD19, CD20, CD22, CD23, CD25, CD29, CD38, CD40L, CD52, CD64, CD83, CD147 or CD154.

When a proinflammatory effector receptor is targeted, in a preferred embodiment the actual target may be an extracellular domain of the proinflammatory effector receptor. This extracellular domain of the proinflammatory effector receptor may be fused to an antibody. More particularly, the proinflammatory effector may be a soluble receptor or receptor ligand which is fused to an antibody. In an alternative embodiment, the composition may comprise at least one molecule reactive with a proinflammatory effector receptor. This molecule may be a natural antagonist for said proinflammatory effector receptor, or a fragment or mutant of this antagonist that interacts specifically with the receptor. In a preferred embodiment, the natural antagonist is the natural IL-1 receptor antagonist, or a fragment or mutant of this antagonist.

One of the at least two different targets to which the multispecific antibody binds specifically may be a target that is not a proinflammatory effector of the immune system or a coagulation factor. In this case the multispecific antibody also binds specifically with at least one proinflammatory effector of the immune system or at least one coagulation factor. In one embodiment, this at least one other target is an antigen or receptor of the adaptive immune system. In other embodiments, the at least one other target of the multispecific antibody targets cells of the innate immune system, such as granulocytes, monocytes, macrophages, dendritic cells, and NK-cells. Other targets include platelets and endothelial cells. Yet another group of targets is the group consisting of C5a, LPS, IFN-γ and B7. A further group of suitable targets include CD2, CD4, CD14, CD18, CD11a, CD20, CD22, CD23, CD25, CD29, CD38, CD40L, CD52, CD64, CD83, CD147, and CD154. The CDs are targets on immune cells, which can be blocked by antibodies to prevent an immune cell response. CD83 is particularly useful as a marker of activated dendritic cells (Cao et al., *Biochem J.*, Aug. 23, 2004 (Epub ahead of print); Zinser et al., *J. Exp Med.* 200(3):345-51 (2004)).

Certain targets are of particular interest, such as MIF, HMGB-1, TNF-α, the complement factors and complement regulatory proteins, and the coagulation factors. MIF is a pivotal cytokine in of the innate immune system and plays an important part in the control of inflammatory responses. Originally described as a T lymphocyte-derived factor that inhibited the random migration of macrophages, the protein known as macrophage migration inhibitory factor (MIF) was an enigmatic cytokine for almost 3 decades. In recent years, the discovery of MIF as a product of the anterior pituitary gland and the cloning and expression of bioactive, recombinant MIF protein have led to the definition of its critical biological role in vivo. MIF has the unique property of being released from macrophages and T lymphocytes that have been stimulated by glucocorticoids. Once released, MIF overcomes the inhibitory effects of glucocorticoids on TNF-α, IL-1β, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. MIF is the first mediator to be identified that can counter-regulate the inhibitory effects of glucocorticoids and thus plays a critical role in the host control of inflammation and immunity. MIF is particularly useful in treating cancer, pathological angiogenesis, and sepsis or septic shock, and therefore a useful target to be combined with anti-histone antibodies of this invention.

HMGB-1, a DNA binding nuclear and cytosolic protein, is a proinflammatory cytokine released by monocytes and macrophages that have been activated by IL-1β, TNF, or LPS. Via its B box domain, it induces phenotypic maturation of DCs. It also causes increased secretion of the proinflammatory cytokines IL-1α, IL-6, IL-8, IL-12, TNF-α and RANTES. HMGB-1 released by necrotic cells may be a signal of tissue or cellular injury that, when sensed by DCs, induces and or enhances an immune reaction. Palumbo et al. report that HMGB-1 induces mesoangioblast migration and proliferation (*J Cell Biol*, 164:441-449 (2004)).

HMGB-1 is a late mediator of endotoxin-induced lethality that exhibits significantly delayed kinetics relate to TNF and IL-1beta. Experimental therapeutics that target specific early inflammatory mediators such as TNF and IL-1 beta alone have not proven efficacious in the clinic, but multispecific antibodies according to the present invention can improve response by targeting both early and late inflammatory mediators, especially when combined with the anti-histone antibodies of this invention.

Multispecific antibodies that target HMBG-1 are especially useful in treating arthritis, particularly collagen-induced arthritis. Multispecific antibodies comprising HMGB-1 also are useful in treating sepsis and/or septic shock. Yang et al., *PNAS USA* 101:296-301 (2004); Kokkola et al., *Arthritis Rheum*, 48:2052-8 (2003); Czura et al., *J Infect Dis*, 187 Suppl 2:S391-6 (2003); Treutiger et al., *J. Intern Med*, 254:375-85 (2003).

TNF-α is an important cytokine involved in systemic inflammation and the acute phase response. TNF-α is released by stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-α after stimulation. Its release is stimulated by several other mediators, such as interleukin-1 and bacterial endotoxin, in the course of damage, e.g., by infection. It has a number of actions on various organ systems, generally together with interleukins-1 and -6. One of the actions of TNF-α is appetite suppression; hence multispecific antibodies for treating cachexia preferably target TNF-α. It also stimulates the acute phase response of the liver, leading to an increase in C-reactive protein and a number of other mediators. It also is a useful target when treating sepsis or septic shock, which is the basis for its being combined with anti-histone antibodies and/or thrombomodulin in such diseases, particularly sepsis and autoimmune diseases.

The complement system is a complex cascade involving proteolytic cleavage of serum glycoproteins often activated by cell receptors. The "complement cascade" is constitutive and non-specific but it must be activated in order to function. Complement activation results in a unidirectional sequence of enzymatic and biochemical reactions. In this cascade, a specific complement protein, C5, forms two highly active, inflammatory byproducts, C5a and C5b, which jointly activate white blood cells. This in turn evokes a number of other inflammatory byproducts, including injurious cytokines, inflammatory enzymes, and cell adhesion molecules. Together, these byproducts can lead to the destruction of tissue seen in many inflammatory diseases. This cascade ultimately results in induction of the inflammatory response, phagocyte chemotaxis and opsonization, and cell lysis.

The complement system can be activated via two distinct pathways, the classical pathway and the alternate pathway. Most of the complement components are numbered (e.g., C1, C2, C3, etc.) but some are referred to as "Factors." Some of the components must be enzymatically cleaved to activate their function; others simply combine to form complexes that are active. Active components of the classical pathway include C1q, C1r, C1s, C2a, C2b, C3a, C3b, C4a, and C4b. Active components of the alternate pathway include C3a, C3b, Factor B, Factor Ba, Factor Bb, Factor D, and Properdin. The last stage of each pathway is the same, and involves component assembly into a membrane attack complex. Active components of the membrane attack complex include C5a, C5b, C6, C7, C8, and C9n. Anti-C5a combined with anti-histone antibodies of this invention is particularly effective for the therapy of coagulopathies and sepsis.

While any of these components of the complement system can be targeted by a multispecific antibody, certain of the complement components are preferred. C3a, C4a and C5a cause mast cells to release chemotactic factors such as histamine and serotonin, which attract phagocytes, antibodies and complement, etc. These form one group of preferred targets according to the invention. Another group of preferred targets includes C3b, C4b and C5b, which enhance phagocytosis of foreign cells. Another preferred group of targets are the predecessor components for these two groups, i.e., C3, C4 and C5. C5b, C6, C7, C8 and C9 induce lysis of foreign cells (membrane attack complex) and form yet another preferred group of targets.

Complement C5a, like C3a, is an anaphylatoxin. It mediates inflammation and is a chemotactic attractant for induction of neutrophilic release of antimicrobial proteases and oxygen radicals. Therefore, C5a and its predecessor C5 are particularly preferred targets. By targeting C5, not only is C5a affected, but also C5b, which initiates assembly of the membrane-attack complex. Thus, C5 is another preferred target. C3b, and its predecessor C3, also are preferred targets, as both the classical and alternate complement pathways depend upon C3b. Three proteins affect the levels of this factor, C1 inhibitor, protein H and Factor I, and these are also preferred targets according to the invention. Complement regulatory proteins, such as CD46, CD55, and CD59, may be targets to which the multispecific antibodies bind.

Coagulation factors also are preferred targets according to the invention, particularly tissue factor (TF), thrombomodulin, and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation.

TF is expressed by various cell types, including monocytes, macrophages and vascular endothelial cells, and is induced by IL-1, TNF-α or bacterial lipopolysaccharides. Protein kinase C is involved in cytokine activation of endothelial cell TF expression. Induction of TF by endotoxin and cytokines is an important mechanism for initiation of disseminated intravascular coagulation seen in patients with Gram-negative sepsis. TF also appears to be involved in a variety of non-hemostatic functions including inflammation, cancer, brain function, immune response, and tumor-associated angiogenesis. Thus, multispecific antibodies that target TF are useful not only in the treatment of coagulopathies, but also in the treatment of sepsis, cancer, pathologic angiogenesis, and other immune and inflammatory dysregulatory diseases according to the invention. A complex interaction between the coagulation pathway and the cytokine network is suggested by the ability of several cytokines to influence TF expression in a variety of cells and by the effects of ligand binding to the receptor. Ligand binding (factor VIIa) has been reported to give an intracellular calcium signal, thus indicating that TF is a true receptor.

Thrombin is the activated form of coagulation factor II (prothrombin); it converts fibrinogen to fibrin. Thrombin is a potent chemotaxin for macrophages, and can alter their production of cytokines and arachidonic acid metabolites. It is of particular importance in the coagulopathies that accompany sepsis. Numerous studies have documented the activation of the coagulation system either in septic patients or following LPS administration in animal models. Despite more than thirty years of research, the mechanisms of LPS-induced liver toxicity remain poorly understood. It is now clear that they involve a complex and sequential series of interactions between cellular and humoral mediators. In the same period of time, gram-negative systemic sepsis and its sequallae have become a major health concern, attempts to use monoclonal antibodies directed against LPS or various inflammatory mediators have yielded only therapeutic failures, as noted elsewhere herein. Multispecific antibodies according to the invention that target both thrombin and at least one other target address the clinical failures in sepsis treatment.

A recombinant form of thrombomodulin has been approved for treatment of disseminated intravascular coagulation (DIC) and is in phase II clinical trials for DIC associated with sepsis (Okamoto et al., 2012, *Crit Care Res Pract*, Epub 2012 Feb. 28). Thrombomodulin has a pivotal role in the protein C system that is important in the pathogensis of sepsis (Levi and Van der Poll, *Minerva Anestesiol* Epub Dec. 17, 2012). Downregulation of thrombomodulin in sepsis causes impaired activation of protein C that is central in the modulation of coagulation and inflammation (Levi and Van der Poll, *Minerva Anestesiol* Epub Dec. 17, 2012). Administration of recombinant thrombomodulin is reported to have a beneficial effect on restoration of coagulation and improvement of organ failure (Levi and Van der Poll, *Minerva Anestesiol* Epub Dec. 17, 2012). A recent retrospective study confirmed that treatment with recombinant thrombomodulin was associated with reduced mortality in hospitalized patients with sepsis-induced DIC (Yamakawa et al., 2013, *Intensive Care Med*, Epub Jan. 30, 2013).

In other embodiments, the multispecific antibodies bind to a MHC class I, MHC class II or accessory molecule, such as CD40, CD54, CD80 or CD86. The multispecific antibody also may bind to a T-cell activation cytokine, or to a cytokine mediator, such as NF-κB.

Targets associated with sepsis and immune dysregulation and other immune disorders include MIF, IL-1, IL-6, IL-8, CD74, CD83, and C5aR. Antibodies and inhibitors against C5aR have been found to improve survival in rodents with sepsis (Huber-Lang et al., *FASEB J* 2002; 16:1567-1574; Riedemann et al., *J Clin Invest* 2002; 110:101-108) and septic shock and adult respiratory distress syndrome in monkeys (Hangen et al., *J Surg Res* 1989; 46:195-199; Stevens et al., J Clin Invest 1986; 77:1812-1816). Thus, for sepsis, one of the at least two different targets preferably is a target that is associated with infection, such as LPS/C5a. Other preferred targets include HMGB-1, TF, CD14, VEGF, and IL-6, each of which is associated with septicemia or septic shock. Preferred multispecific antibodies are those that target two or more targets from HMGB-1, TF and MIF, such as MIF/TF, and HMGB-1/TF, as well as HMGB-1 and histone, and MIF and histone.

In still other embodiments, one of the at least two different targets may be a target this is associated with graft versus host disease or transplant rejection, such as MIF (Lo et al., *Bone Marrow Transplant*, 30(6):375-80 (2002)). One of the at least two different targets also may one that associated with acute respiratory distress syndrome, such as IL-8 (Bouros et al., *PMC Pulm Med*, 4(1):6 (2004), atherosclerosis or restenosis, such as MIF (Chen et al., *Arterioscler Thromb Vasc Biol*, 24(4):709-14 (2004), asthma, such as IL-18 (Hata et al., *Int Immunol, Oct.* 11, 2004 Epub ahead of print), a granulomatous disease, such as TNF-α (Ulbricht et al., *Arthritis Rheum*, 50(8):2717-8 (2004), a neuropathy, such as carbamylated EPO (erythropoietin) (Leist et al., *Science* 305(5681):164-5 (2004), or cachexia, such as IL-6 and TNF-α.

Other targets include C5a, LPS, IFN-gamma, B7; CD2, CD4, CD14, CD18, CD11a, CD11b, CD11c, CD14, CD18, CD27, CD29, CD38, CD40L, CD52, CD64, CD83, CD147, CD154. Activation of mononuclear cells by certain microbial antigens, including LPS, can be inhibited to some extent by antibodies to CD18, CD11b, or CD11c, which thus implicate β.sub.2-integrins (Cuzzola et al., *J Immunol* 2000; 164:5871-5876; Medvedev et al., J Immunol 1998; 160: 4535-4542). CD83 has been found to play a role in giant cell arteritis (GCA), which is a systemic vasculitis that affects medium- and large-size arteries, predominately the extracranial branches of the aortic arch and of the aorta itself, resulting in vascular stenosis and subsequent tissue ischemia, and the severe complications of blindness, stroke and aortic arch syndrome (Weyand and Goronzy, *N Engl J Med* 2003; 349:160-169; Hunder and Valente, In: Inflammatory Diseases of Blood Vessels. G. S. Hoffman and C. M. Weyand, eds, Marcel Dekker, New York, 2002; 255-265). Antibodies to CD83 were found to abrogate vasculitis in a SCID mouse model of human GCA (Ma-Krupa et al., *J Exp Med* 2004; 199:173-183), suggesting to these investigators that dendritic cells, which express CD83 when activated, are critical antigen-processing cells in GCA. In these studies, they used a mouse anti-CD83 Mab (IgG1 clone HB15e from Research Diagnostics). CD154, a member of the TNF family, is expressed on the surface of CD4-positive T-lymphocytes, and it has been reported that a humanized monoclonal antibody to CD 154 produced significant clinical benefit in patients with active systemic lupus erythematosus (SLE) (Grammar et al., *J Clin Invest* 2003; 112:1506-1520). It also suggests that this antibody might be useful in other autoimmune diseases (Kelsoe, *J Clin Invest* 2003; 112:1480-1482). Indeed, this antibody was also reported as effective in patients with refractory immune thrombocytopenic purpura (Kuwana et al., *Blood* 2004; 103:1229-1236).

In rheumatoid arthritis, a recombinant interleukin-1 receptor antagonist, IL-1Ra or anakinra (Kineret®), has shown activity (Cohen et al., *Ann Rheum Dis* 2004; 63:1062-8; Cohen, *Rheum Dis Clin North Am* 2004; 30:365-80). An improvement in treatment of these patients, which hitherto required concomitant treatment with methotrexate, is to combine anakinra with one or more of the anti-proinflammatory effector cytokines or anti-proinflammatory effector chemokines (as listed above). Indeed, in a review of antibody therapy for rheumatoid arthritis, Taylor (*Curr Opin Pharmacol* 2003; 3:323-328) suggests that in addition to TNF, other antibodies to such cytokines as IL-1, IL-6, IL-8, IL-15, IL-17 and IL-18, are useful.

There are certain advantages when the multispecific antibody is an antibody that is at least bispecific, including rapid clearance from the blood. For example, the bispecific antibody may bind to a receptor or to its target molecule, such as for LPS, IL-1, IL-10, IL-6, MIF, HMGB1, TNF, IFN, tissue factor, thrombin, CD14, CD27, and CD134. Many of these exist as both receptors and as soluble forms in the blood. Binding by the bispecific antibodies results in rapid clearance from the blood, and then targeting by the second arm of the fusion protein to another cell, such as a macrophage, for transport and degradation by the cell, especially the lysosomes. This is particularly effective when the second targeting arm is against an internalizing antigen, such as CD74, expressed by macrophages and dendritic cells. This is consistent with the invention of Hansen, U.S. Pat. No. 6,458,933, but focusing herein on inflammatory cytokines and other immune modulation molecules and receptors for immune-dysregulation diseases, and cancer antigens for the immunotherapy of these cancers.

Preferred multispecific antibodies for the treatment of cancer include antibodies to CD55 and to any of the cancer antigens identified above, antibodies to CD46 and to any of the above cancer antigens, antibodies to CD59 and to any of the above cancer antigens, antibodies to MIF and to any of the above cancer antigens, antibodies to NF-κB and any of the above cancer antigens, and antibodies to IL-6 and to any of the above cancer antigens other than IL-6. These multispecific antibodies for treating cancer may be antibody combinations or fusion proteins, given together or separately.

The multispecific antibody or antibody combination may be used in conjunction with one or more secondary therapeutics. This secondary therapeutic may be one that affects a component of the innate immune system. Alternatively, it may affect a component of the adaptive immune system. The secondary therapeutic may also be a component that affects coagulation, cancer, or an autoimmune disease, such as a cytotoxic drug.

The multispecific antibody may react specifically with targets or markers associated with specific diseases and conditions, such as infectious diseases, acute respiratory distress syndrome, septicemia or septic shock, graft versus host disease or transplant rejection, atherosclerosis, asthma, acne, giant cell arteritis, a granulomatous disease, a neuropathy, cachexia, a coagulopathy such as diffuse intravascular coagulation (DIC), or myocardial ischemia.

The multispecific antibodies or antibody combinations are useful in treating conditions such as inflammatory or immune-dysregulatory disorders, pathologic angiogenesis or cancer, and infectious disease. The composition can be used to treat septicemia or septic shock, infectious disease (bacterial, viral, fungal, or parasitic), neuropathy, graft versus host disease or transplant rejection, acute respiratory distress syndrome, a granulomatous disease, asthma, atherosclerosis, acne, giant cell arteritis, coagulopathies such as diffuse intravascular coagulation (DIC), or cachexia. In other embodiments, the condition is an autoimmune disease, especially a Class III autoimmune diseases.

The composition also can be used to treat a pathologic angiogenesis or cancer. The cancer may be hematopoietic cancer, such as leukemia, lymphoma, or myeloma, etc. Alternatively, the cancer may be a solid tumor, such as a carcinoma, melanoma, sarcoma, glioma, etc.

The subject antibody may be an immunoconjugate that comprises a therapeutic agent, such as a radionuclide, an immunomodulator, a hormone, a hormone antagonist, an enzyme, an enzyme inhibitor, oligonucleotide, a photoactive therapeutic agent, a cytotoxic agent, an antibody, an angiogenesis inhibitor, an immune modulator, and a combination thereof. When the therapeutic agent is an oligonucleotide it may be an antisense oligonucleotide. Therapeutic agents are discussed above in more detail.

The present invention also provides a method of treating a condition selected from an inflammatory or immune-dysregulatory disorders, a pathologic angiogenesis or cancer, and an infectious disease, comprising administering a therapeutically effective amount of a multispecific antibody that includes a hapten binding site, to a patient that is suspected of having such a condition; permitting the multispecific antibody to accrete at target sites; waiting for circulating multispecific antibody to clear from the bloodstream; administering to said subject a hapten that comprises a therapeutic agent; and allowing the hapten with the therapeutic agent to bind to the hapten binding site of said multispecific antibody. Preferably, the multispecific antibody has an anti-histone antibody as described in this invention as one of the included antibodies.

The multispecific antibodies described herein are useful for treatment of autoimmune diseases, particularly for the treatment of Class III autoimmune diseases including immune-mediated thrombocytopenias, such as acute idiopathic thrombocytopenic purpura and chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

The multispecific antibodies also are useful in treating inflammatory or immune-dysregulatory disorders other than autoimmune disease. Examples of these other inflammatory or immune-dysregulatory disorders that can be treated with composition according to the invention include septicemia or septic shock, infection, neuropathies, graft versus host disease, transplant rejection, acute respiratory distress syndrome, granulomatous disease, asthma, acne, diffuse intravascular coagulation (DIC), and atherosclerosis.

The multispecific antibodies also can be used in treating inflammation associated with an infectious disease, including viral infections, bacterial infections, parasitic infections, and fungal infections. Exemplary viruses include the species of human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus. Exemplary bacteria include *Anthrax bacillus, Streptococcus agalactiae, Legionella pneumophilia, Streptococcus pyogenes, Escherichia coli, Neisseria gonorrhoeae, Neisseria meningitidis, Pneumococcus, Hemophilis influenzae B, Treponema pallidum*, Lyme disease spirochetes, *Pseudomonas aeruginosa, Mycobacterium leprae, Brucella abortus, Mycobacterium tuberculosis* and *Clostridium tetani*. Exemplary protozoans are *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* or *Mesocestoides corti*. Exemplary mycoplasma are *Mycoplasma arthritidis, Mycoplasma hyorhinis, Mycoplasma orale, Mycoplasma arginini, Acholeplasma laidlawii, Mycoplasma salivarum*, and *Mycoplasma pneumoniae*. The fungus may be from the species of *Microsporum, Trichophyton, Epidermophyton, Sporothrix schenckii, Cyrptococcus neoformans, Coccidioides immitis, Histoplasma capsulatum, Blastomyces dermatitidis*, or *Candida albicans*. Exemplary parasites include malarial parasites, spirochetes and the like, including helminthes. Listings of representative disease-causing infectious organisms to which antibodies can be developed for use in this invention are contained in the second and subsequent editions of Davis et al., MICROBIOLOGY (Harper & Row, New York, 1973 and later), and are well known to one of ordinary skill in the art. In these embodiments, the multispecific antibody preferably targets an antigen associated with the microbe or parasite.

Sepsis and septic shock are characterized by overwhelming inflammatory and immune responses, which make them particularly susceptible to treatment with multispecific antibodies according to the present invention. Treatment of these conditions according to the present invention entails combining agents that work via different mechanisms, and preferably by administering fusion proteins of antagonist or agonist mediators or antibodies which function against more than one target molecule involved in the pathogenesis of this immune dysregulatory, inflammatory disease. As advocated by Van Amersfoort et al. (ibid.), "an attempt should be made to restore the balance between the pro- and anti-inflammatory responses." The present invention restores the balance and provides a clear improvement art over the use of single agents that neutralize the proinflammatory cytokines, such TNF or IL-1, in patients with sepsis, by using multispecific antibodies specific for at least two different targets, where the targets are selected from the group consisting of proinflammatory effectors of the innate immune system, coagulation factors, and targets specifically associated with sepsis or septic shock. More preferably, the multispecific construct contains an anti-histone antibody (or fragment), as provided in this invention.

In one embodiment for treatment of sepsis or septic shock, different anti-inflammatory agents are combined with activated protein C, as well as with anti-coagulation agents, such as thrombomodulin, and at least one component of this multiple agent therapy is an agonist or antagonist antibody to at least one target receptor or mediator of inflammation or coagulation, including complement pathway antagonists, and more preferably an anti-histone antibody as provided in this invention. A listing of selected anti-inflammatory and immunomodulating agents used to treat patients with severe sepsis and septic shock is found in Bochud and Calandra (*Brit Med J* 2003; 326:262-266), and clinical trials of most of these immunomodulatory therapies of severe sepsis and septic shock are reviewed in Vincent et al., *Clin Infect Dis* 2002; 34:1084-93.

Particularly preferred agents useful in treatment of sepsis and septic shock are multispecific antibodies that target MIF, LPS, TNF-α, C5a, C5a receptor (C5aR), TLR2 or HMGB-1 as one of the targets. The other target can also be selected from these, as well as from other proinflammatory cytokines or receptors, such as interleukin IL-1, TSST-1 (toxic shock syndrome toxin 1), NCA-90, NCA-95, and HLA-DR. Preferred combinations of agents or fusion proteins for treatment of severe sepsis or septic shock include those that target MIF and C5a receptor (C5aR), MIF and IL-6, LPS and MIF, TNF-α and HMGB-1, TLR2 (toll-like receptor-2) and LPS, TLR2 and IL-6, TLR2 and C5aR. An anti-MIF/anti-NCA-90 or an anti-MIF/anti-HLA-DR multispecific antibody can be used to target granulocytes in blood/infectious deposits to neutralize MIF in patients with early evidence of toxic shock. These combinations can also include anti-histone antibodies, as described herein, in various combinations, such as with antibodies against MIF, IL-6, C5a, TNF-alpha, LPS, or HMGB-1. Antibodies against CD74, such as milatuzumab, may also be combined with anti-histone antibodies, as described herein, for improved therapy of various inflammatory, immune dysregulatory, or malignant (cancerous) diseases. Still more preferable, for sepsis and septic shock therapy (and the induced disseminated intravascular coagulation), is the addition of thrombomodulin [rhTM] (such as recombinant human soluble thrombomodulin (Yamakawa, *Intensive Care Med* 2013; published online 30 Jan. 2013; DO1 10.1007/s00134-013-2822-2). Preferably the antibody structures are humanized or human antibody constructs. These are readily combined or constructed by those of skill in the art from available antibodies. For example, T2.5 Mab has been developed as an antagonist to TLR-2 by immunizing a TLR2-neg mouse with TLR2 extracellular domain, and this antibody inhibits release of inflammatory mediators, such as TNF-α and prevents lethal shock-like syndrome in mice (Meng et al., *J Clin Invest* 2004; 113:1473-1481). In preferred embodiments, recombinant activated protein C is used as a secondary therapeutic in combination with antibody mixtures and fusion proteins. Likewise, as discussed, recombinant thrombomodulin is also used as a secondary therapeutic in combination with antibody mixtures and fusion proteins.

It also has been discovered that multispecific antibodies which target both a complement regulatory factor such as CD46, CD55, and/or CD59 and a tumor-associated antigen, and more particularly at least bispecific antibodies in which one arm targets the complement regulatory factor and a second arm targets an tumor associated antigen, are more effective in treating cancer than antibodies that target just one of these antigens. Moreover, contrary to the teaching of Sier et al., supra, it has been discovered that the use of beta-glucan is not obligatory in vivo for the improved efficacy of a such a multispecific antibody over the use of the anticancer antibody alone, and that the bispecific antibody targeting the cancer and the complement-regulatory protein (e.g., CD55) increases cancer cell killing over either antibody used by itself, specifically against tumors that have a high expression of the complement-regulatory protein (thus blocking complement-mediated cytotoxicity by antibodies).

Another preferred complement-related target for neutralizing antibodies is complement factor H (and its variant FHL-1) involved in the alternative pathway for complement, especially since factor H may be overexpressed by some cancers (Ajona et al., *Cancer Res* 2004; 64:6310-6318, and references cited therein). Therefore, use of multispecific antibodies, and particularly multispecific antibodies, directed against complement factor H and factor FHL-1 are of particular importance. Multispecific antibodies against complement factor H and its variant FHL-1 additionally may target CD55, CD46 and/or CD59, as well as other complement factors. The targeting of these multispecific antibodies and to tumor-associated antigens and receptors has been found to enhance specific targeting of complement antibodies to the tumor cells, and to provide an advantage over use of antibodies targeting a single antigen or epitope. This has overcome the inconsistencies in the literature published to date.

In non-malignant conditions, there is a different approach. This includes neutralization or interference with other complement receptors or factors, including complement-derived anaphylatoxin C5a or complement-receptor 3 (CR3, CD18/11b), which can mediate adhesion of inflammatory cells to the vascular endothelium. In such situations, increased expression of CD46, CD55, and/or CD59 is desired in order to mitigate complement-mediated immunity, and also to reduce hyperacute rejection, as in organ transplant-rejection. Therefore, use of agonists of such complement regulatory factors would be advantageous.

Particularly preferred agents useful in treatment of atherosclerosis are multispecific antibodies that target MIF, low-density lipoprotein (LDL), and CEACAM6 (e.g., NCA-90). The other target can also be selected from these, as well as from other proinflammatory cytokines. Preferred combinations of agents or fusion proteins for treatment of atherosclerosis target MIF and low-density lipoprotein-modified epitopes, NCA-90 and MIF, NCA-90 and low-density lipoprotein (LDL) epitopes, or LDL and CD83. There are readily combined or constructed by those of skill in the art from commercially available antibodies. For example, Mab MDA2, a prototype Mab, recognizes malondialdehyde-lysing epitopes (e.g., in malondialdehyde-modified LDL) within oxidation-rich atherosclerotic lesions (as described by Tsimikas et al., *J Nucl Cardiol* 1999; 6:81-90).

In addition to sepsis and atherosclerosis, MIF has been reported to be expressed in rabbits with atherogenesis (Lin et al., *Circulation Res* 2000; 87:1202-1208), indicating that it is a key cytokine for this condition. Other diseases in which MIF has been implicated include glomerulonephritis, arthritis, delayed-type hypersensitivity, gastric inflammation, and acute myocardial ischemia (reviewed by Yu et al., *J Histochem Cytochem* 2003; 625-631). Multispecific antibodies that target MIF are therefore useful in treating any of these conditions.

As many as 500,000 individuals in the U.S. develop sepsis each year, a number that is rising with the aging of the population. Despite the best in antibiotic therapy and cardiopulmonary support, and the advances in understanding of inflammation and coagulation in sepsis, as many as half these cases are fatal. During infection, pro-inflammatory cytokines are released and activated. These include TNF-α, IL-1, and IL-6. Anti-inflammatory mediators, including IL-4 and IL-10, appear insufficient to regulate pro-inflammatory cytokines in severe sepsis.

Prominent features of the septic response include uncontrolled inflammation and coagulation. Vascular endothelial damage is the triggering event, whether caused by endotoxin, tissue factor, necrotic cells, or amniotic fluid, becomes the triggering event. This endothelial damage leads to release of tissue factor, which activates the coagulation system resulting in excess thrombin generation. Subsequent clot formation promotes microvascular endothelial dysfunction, and, if unchecked, hypoxemia, organ dysfunction, and organ failure ensue.

Endothelial damage and a shift towards a prothrombotic milieu lead to decreased expression and impaired function of endothelial receptors for thrombin, i.e., thrombomodulin, and protein C, i.e., the endothelial protein C receptor (EPCR). Both thrombomodulin and EPCR are required for the conversion of protein C to its active form, APC. Thus, a major system for the regulation of thrombin formation, clot propagation, and protein C activation is lost.

Nearly all patients with severe sepsis are deficient in protein C. Low protein C levels are associated with shock and poor outcomes, including ICU stay, ventilator dependence, and mortality. Supplying activated protein C exogenously in severe sepsis helps to restore regulation of inflammatory and coagulation responses in some patients, leading to a favorable survival benefit. However, there is an obvious need for new therapeutic modalities to reduce the procoagulant response, and prevent septic organ injury. A preferred secondary therapy is recombinant human thrombomodulin (Yamakawa, 2013).

It has been established that blocking initiation of the procoagulant response before sepsis decreases mortality in nonhuman primates. Effective strategies to block initiation of extrinsic coagulation have included use of monoclonal antibodies to TF, the natural TF pathway inhibitor, and inactive analogs of FVIIa. In a recent study in baboons, it was demonstrated that blockade of the TF-VIIa complex with FVIIai at the onset of sepsis attenuated sepsis-induced multiple organ injury and dramatically protected the lungs and kidneys. Antagonists that inhibit complement activation products, especially the anaphylatoxins, also offer promise to decrease sepsis mortality. C3a, C4a and C5a, appear during sepsis, and the elevated anaphylotoxin plasma levels highly correlate with the development of multiorgan failure. In sepsis, complement may directly promote procoagulant activity or indirectly induce cytokine production. In vitro C5a and the terminal complex of complement, C5b-9, induce tissue factor expression on endothelial cells and monocytes, and assembly of C5b-9 on the surface of platelets has been shown to stimulate prothrombinase activity. The present invention provides improved therapeutics for treating sepsis by providing multispecific antibodies that target two or more of coagulation factors, proinflammatory cytokines and complement activations products.

The multispecific antibodies according to the invention bind to various immune or other host cells involved in the generation of inflammation and other immune-dysregulatory diseases (including intravascular coagulation and myocardial ischemia). They also can be used to enhance a host's immune response to cancer for cancer therapy or prevention. In addition, compositions and treatment methods are provided for neutralizing microbial toxins, such as LPS, neutralizing pro-inflammatory cytokines, and for overcoming abnormalities of coagulation. The methods use appropriate antibody combinations and fusion proteins directed against different participating factors in the cascade leading to severe sepsis, septic shock, and various other immune-dysregulatory diseases.

Although unconjugated multispecific antibodies and antibody fragments and mixtures of unconjugated antibodies and antibody fragments are the preferred, primary therapeutic compositions for therapy according to the invention, the efficacy of such therapy can be enhanced by supplementing the multispecific antibodies with other therapies described herein. In such multimodal regimens, the supplemental therapeutic compositions can be administered before, concurrently or after administration of the multispecific antibodies. For example, multimodal therapy of Class M autoimmune diseases may comprise co-administration of therapeutics that are targeted against T-cells, plasma cells or macrophages, such as antibodies directed against T-cell epitopes, more particularly against the CD4 and CD5 epitopes. Gamma globulins also may be co-administered. In some cases, it may be desirable to co-administer immunosuppressive drugs such as corticosteroids and possibly also cytotoxic drugs. In this case, lower doses of the corticosteroids and cytotoxic drugs can be used as compared to the doses used in conventional therapies, thereby reducing the negative side effects of these therapeutics. When the disease to be treated is cancer, the use of various chemotherapeutic drugs, naked antibodies used in immunotherapy, and radiation (external or internal), can be combined with therapy according to the invention. Likewise, when infection and/or septicemia or septic shock are being treated, antimicrobial drugs may be used in combination with the multispecific antibodies.

Methods of Therapeutic Treatment

In various embodiments, antibodies or antigen-binding antibody fragments, either alone or in combination with one or more other therapeutic agents may be utilized. In certain embodiments, the antibodies or fragments thereof may be naked antibodies or fragments, that are not conjugated to any other therapeutic agents. In alternative embodiments, the antibodies or fragments may be immunoconjugates that are covalently attached to one or more therapeutic and/or diagnostic agents.

Various embodiments concern methods of treating a cancer in a subject, such as a mammal, including humans, domestic or companion pets, such as dogs and cats, comprising administering to the subject a therapeutically effective amount of a cytotoxic immunoconjugate.

In one embodiment, immunological diseases which may be treated with the subject anti-histone antibodies may include, for example, joint diseases such as ankylosing spondylitis, juvenile rheumatoid arthritis, rheumatoid arthritis; neurological disease such as multiple sclerosis and myasthenia gravis; pancreatic disease such as diabetes, especially juvenile onset diabetes; gastrointestinal tract disease such as chronic active hepatitis, celiac disease, ulcerative colitis, Crohn's disease, pernicious anemia; skin diseases such as psoriasis or scleroderma; allergic diseases such as asthma and in transplantation related conditions such as graft versus host disease and allograft rejection.

The administration of the cytotoxic immunoconjugates can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5AC, Ia, MIF, HM1.24, HLA-DR, tenascin, Flt-3, VEGFR, PlGF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., Cancer Res. 48:2610 (1988); Hekman et al., Cancer Immunol. Immunother. 32:364 (1991); Longo, Curr. Opin. Oncol. 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,501,498; 7,612,180; 7,670,804; and U.S. Patent Application Publ. Nos. 20080131363; 20070172920; 20060193865; and 20080138333, the Examples section of each incorporated herein by reference.

The anti-histone antibody therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., Eur. J. Haematol. 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, lenalidomide and bryostatin-1.

The subject anti-histone antibodies can be formulated according to known methods to prepare pharmaceutically useful compositions, whereby the anti-histone antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The subject anti-histone antibodies can be formulated for intravenous administration via, for example, bolus injection or continuous infusion. Preferably, the anti-histone antibody is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the anti-histone antibodies. Control release preparations can be prepared through the use of polymers to complex or adsorb the anti-histone antibodies. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release from such a matrix depends upon the molecular weight of the anti-histone antibody, the amount of anti-histone antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The anti-histone antibody may also be administered to a mammal subcutaneously or even by other parenteral routes. Moreover, the administration may be by continuous infusion or by single or multiple boluses. Preferably, the anti-histone antibody is infused over a period of less than about 4 hours, and more preferably, over a period of less than about 3 hours.

More generally, the dosage of an administered anti-histone antibody for humans will vary depending upon such factors as the patient's age, weight, height, sex, general medical condition and previous medical history. It may be desirable to provide the recipient with a dosage of anti-histone antibody that is in the range of from about 0.1 mg/kg to 25 mg/kg as a single intravenous infusion, although a lower or higher dosage also may be administered as circumstances dictate. A dosage of 0.1-20 mg/kg for a 70 kg patient, for example, is 7-1,400 mg, or 4-824 mg/m$^2$ for a 1.7-m patient. The dosage may be repeated as needed, for example, once or twice per week for 4-10 weeks, once per week for 8 weeks, or once per week for 4 weeks. It may also be given less frequently, such as every other week for several months, or monthly or quarterly for many months, as needed in a maintenance therapy.

Alternatively, an anti-histone antibody may be administered as one dosage every 2 or 3 weeks, repeated for a total of at least 3 dosages. Or, the construct may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 10 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule In preferred embodiments, the anti-histone antibodies are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Expression Vectors

Still other embodiments may concern DNA sequences comprising a nucleic acid encoding an antibody, antibody fragment, toxin or constituent fusion protein of an anti-histone antibody, such as a DNL® construct. Fusion proteins may comprise an antibody or fragment or toxin attached to, for example, an AD or DDD moiety.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327 and 7,537,930, the Examples section of each incorporated herein by reference.

Autoimmune Disease

Exemplary autoimmune or immune dysfunction diseases include acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjögren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, fibrosing alveolitis, graft-versus-host disease (GVHD), organ transplant rejection, sepsis, septicemia and inflammation.

Kits

Various embodiments may concern kits containing components suitable for treating or diagnosing diseased tissue in a patient. Exemplary kits may contain one or more anti-histone antibodies as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Example 1. General Techniques for Construction of Anti-Histone Antibodies

The Vκ (variable light chain) and $V_H$ (variable heavy chain) sequences for anti-histone antibodies may be obtained by a variety of molecular cloning procedures, such as RT-PCR, 5'-RACE, and cDNA library screening. Specifically, the V genes of an anti-histone MAb from a cell that expresses a murine anti-histone MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized anti-histone MAb can then be designed and constructed as described by Leung et al. (*Mol. Immunol.*, 32: 1413 (1995)).

cDNA can be prepared from any known hybridoma line or transfected cell line producing a murine anti-histone MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)).

PCR reaction mixtures containing 10 μl of the first strand cDNA product, 10 μl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), 250 μM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified Vκ and VH fragments can be purified on 2% agarose (BioRad, Richmond, Calif.). The humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for $V_H$ can be subcloned into a similar staging vector, such as the pBluescript-based VHpBS. Individual clones containing the respective PCR products may be sequenced by, for example, the method of Sanger et al. (*Proc. Natl. Acad. Sci.*, USA, 74: 5463 (1977)).

Expression cassettes containing the Vκ and $V_H$ sequences, together with the promoter and signal peptide sequences, can be excised from VKpBR and VHpBS, respectively, by double restriction digestion as HindIII-BamHI fragments. The Vκ and $V_H$ expression cassettes can be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric, humanized or human anti-histone MAb by, for example, an ELISA assay. Alternatively, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. (*J. Immunol. Methods* 125:191 (1989) and also shown in Losman et al., Cancer, 80:2660 (1997)). Another vector that is useful is the GS vector, as described in Barnes et al., *Cytotechnology* 32:109-123 (2000). Other appropriate mammalian expression systems are described in Werner et al., Arzneim.-Forsch./Drug Res. 48(II), Nr. 8, 870-880 (1998).

Co-transfection and assay for antibody secreting clones by ELISA, can be carried out as follows. About 10 μg of VKpKh (light chain expression vector) and 20 μg of VHpG1g (heavy chain expression vector) can be used for the transfection of $5 \times 10^6$ SP2/0 myeloma cells by electroporation (BioRad, Richmond, Calif.) according to Co et al., *J. Immunol.*, 148: 1149 (1992). Following transfection, cells may be grown in 96-well microtiter plates in complete HSFM medium (Life Technologies, Inc., Grand Island, N.Y.) at 37° C., 5% $CO_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis. Transfectoma clones that are positive for the secretion of chimeric, humanized or human heavy chain can be identified by ELISA assay.

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2μ membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by ELISA and its concentration adjusted to about 1 mg/ml using PBS. Sodium azide, 0.01% (w/v), is conveniently added to the sample as preservative.

Example 2. Production of Chimeric IMMU-H4 (cIMMU-H4) Antibody

A chimeric form of the anti-H4 IMMU-H4 antibody was produced as discussed in Example 1 above. The variable region sequences used were as disclosed in SEQ ID NO:98 and SEQ ID NO:99. The human heavy chain constant region sequence used was as disclosed in SEQ ID NO:86. The human light chain kappa constant region sequence was as disclosed in FIG. 7B of U.S. Pat. No. 7,151,164 (incorporated herein by reference). The purity of the cIMMU-H4 antibody was confirmed by SE-HPLC chromatography (not shown).

Representative data showing the binding affinity of cIMMU-H4 produced from a selected clone (4C3) are provided in FIG. 7. Surprisingly, the cIMMU-H4 (4C3) has a higher binding affinity ($K_D$=0.96 nM) for histones than its murine counterpart ($K_D$=6.6 nM) based on ELISA. These surprising and unexpected results illustrate the superiority of chimeric and humanized anti-histone antibodies compared to the parental murine antibodies.

Example 3. Production of Humanized IMMU-H4 Antibody

A humanized form of the anti-H4 IMMU-H4 antibody is produced according to Leung et al., (1995, Molec Immunol 32:1413-27). The variable region sequences used are as disclosed in SEQ ID NO:98 an6 SEQ ID NO:97. The human heavy chain constant region sequence used is as disclosed in SEQ ID NO:86. The human light chain kappa constant region sequence is as disclosed in FIG. 7B of U.S. Pat. No. 7,151,164 (incorporated herein by reference).

The binding characteristics of the humanized IMMU-H4 antibody are identical to those of the chimeric IMMU-H4 antibody.

Example 4. Production of Chimeric IMMU-H3 Antibody

A chimeric form of the anti-H3 IMMU-H3 antibody is produced as discussed in Example 1 above. The variable region sequences used are as disclosed in SEQ ID NO:108 and SEQ ID NO:109. The human heavy chain constant region sequence used is as disclosed in SEQ ID NO:86. The human light chain kappa constant region sequence is as disclosed in FIG. 7B of U.S. Pat. No. 7,151,164 (incorporated herein by reference). The chimeric IMMU-H3 antibody competes for binding to H3 with, and binds to the same epitope of H3 as, the parental murine antibody.

Example 5. Production of Humanized IMMU-H3 Antibody

A humanized form of the anti-H3 IMMU-H3 antibody is produced according to Leung et al., (1995, Molec Immunol 32:1413-27). The variable region sequences used are as disclosed in SEQ ID NO:106 and SEQ ID NO:107. The human heavy chain constant region sequence used is as disclosed in SEQ ID NO:86. The human light chain kappa constant region sequence is as disclosed in FIG. 7B of U.S. Pat. No. 7,151,164 (incorporated herein by reference).

The binding characteristics of the humanized IMMU-H3 antibody are identical to those of the chimeric IMMU-H3 antibody.

Example 6. Production of Chimeric IMMU-H2B Antibody

A chimeric form of the anti-H2B IMMU-H2B antibody is produced as discussed in Example 1 above. The variable region sequences used are as disclosed in SEQ ID NO:118 and SEQ ID NO:119. The human heavy chain constant region sequence used is as disclosed in SEQ ID NO:86. The human light chain kappa constant region sequence is as disclosed in FIG. 7B of U.S. Pat. No. 7,151,164 (incorporated herein by reference). The chimeric IMMU-H2B antibody competes for binding to H2B with, and binds to the same epitope of H2B as, the parental murine antibody.

Example 7. Production of Humanized IMMU-H2B Antibody

A humanized form of the anti-H2B IMMU-H2B antibody is produced according to Leung et al., (1995, Molec Immunol 32:1413-27). The variable region sequences used are as disclosed in SEQ ID NO:116 and SEQ ID NO:117. The human heavy chain constant region sequence used is as disclosed in SEQ ID NO:86. The human light chain kappa constant region sequence is as disclosed in FIG. 7B of U.S. Pat. No. 7,151,164 (incorporated herein by reference).

The binding characteristics of the humanized IMMU-H2B antibody are identical to those of the chimeric IMMU-H2B antibody.

Example 8. Treatment of Septic Shock

M. N. is a 62-year-old white male with a history of chronic lymphocytic leukemia having past therapy with various cytotoxic drugs, corticosteroids, as well as rituximab and bendamustine, and presenting with stable disease and a past history of several infections that required prolonged antibiotic therapy. He is admitted to the emergency department after being evaluated by his family physician as having symptoms of sepsis, with high temperature (40.7° C.), chills, dyspnea, palpitations, agitation, some confusion, nausea, and cool extremities. Examination reveals tachycardia (>100/min), hypotension (95/55 mm Hg), especially upon standing, and a reduced urine output (800 mL/d), and signs of pneumonia. Tests show a low oxygen tension and acidosis, a blood count not detecting infection, but instead neutropenia (2,500 WBC/mL, with 10% bands), platelets of 38,000, Hg of 6 g/dL, chest x-ray showing a generalized pneumonia, blood tests indicate reduced renal function, with abnormal serum creatinine (3 mg/dL) and elevated BUN levels, and elevated serum lactate indicating tissue hypoperfusion. Blood cultures reveal the presence of S. aureus and Gram-negative bacteria, supporting the diagnosis of septicemia. The patient also has laboratory evidence of a coagulopathy presenting as sepsis-induced disseminated intravascular coagulation (DIC), particularly affecting the extremities and his lungs. The patient is treated in the intensive care unit for severe sepsis and septic shock, which includes general supportive care (oxygen), hemodynamic support by fluid infusion to restore circulating blood volume (500 mL 0.9% sodium chloride and lactated Ringer solution, with up to 2.5 L given over first few hours), vasopressor supportive therapy with dopamine (Intropin, 3 mcg/kg/min iv), and antibiotic therapy with 400 mg IV every 12 hrs of ciprofloxacin (Cipro). The patient is also given recombinant human thrombomodulin (Recomodulin®) at 0.06 mg/kg per day, for a period of 6 days. Five days after admission, the patient is stable but does not show any significant improvement in signs or symptoms, only slightly better urine excretion, a small rise in blood pressure, a small drop in temperature to 39.3° C. and an improvement of his International Society of Thrombosis and Hemostasis (ISTH) DIC scores, including improvement in platelet count, prothrombin time, and fibrinogen level. The evidence of respiratory tract hemorrhage also appears to improve slightly, also with a reduction of his dyspnea. The patient is then given a combination of two humanized monoclonal antibodies sequentially twice weekly for 3 weeks, consisting of 300 mg humanized anti-MIF and 400 mg chimeric anti-histone (IMMU-H4), both by slow infusions over 4 hrs. On week 5 thereafter, the patient shows less confusion, a further drop in temperature, reduction of tachycardia, dyspnea, further improvement of DIC signs, and reduced pneumonia by both physical exam and chest x-ray. At the end of the 6th week, his renal function tests also show some improvement (BUN and serum creatinine values), and he is removed from the intensive care unit to an infectious disease bed, with supportive care adjusted. Two months later, the patient receives a repeated cycle of thrombomodulin and the humanized anti-MIF and chimeric anti-histone antibodies, as well as a repeated course of a broad-spectrum antibiotic, and then shows further improvement so that he becomes ambulatory and has virtually normal mental function and an overall 70+% reduction of pneumonia and a fever of 38° C., and about an 85% normal urine output.

Example 9. Therapy of Systemic Lupus Erythematosus (SLE)

B. S. is a 35-year-old African-American female diagnosed 2 years earlier with SLE, when she presented with a globerulonephritis (WHO grade 3), serositis, polyarthritis, and a vasculitic rash. She had prior therapy with corticosteroids (range of 15-60 mg prednisone per day) and hyrdoxychloroquine (200 mg/day), and at a later time also azathioprine (100 mg/day) and a course of methotrexate because of persistent disease. Over the years, she experiences flares of her SLE, presenting with polyarthritis, lethargy, skin rash, and serositis. She now presents with persistently active disease (BILAG A for musculoskeletal and BILAG B for cardiorespiratory systems, and BILAG C for other systems) and unresponsive to conventional therapies, but is maintained on 40 mg prednisone daily. She is given humanized anti-CD22 monoclonal antibody, epratuzumab, at 600 mg i.v. over 1 hr, repeated once in each of the following four weeks. Four weeks after the third infusion, her circulating B-lymphocytes are reduced by 40% from baseline prior to therapy, but her Hg level has risen from 8 g/dL to 10 g/dL. Her rash and polyarthritis show some improvement, and her musculoskeletal system BILAG A level is reduced to BILAG B, yet she requires additional therapy. At 8 weeks following her anti-CD22 antibody therapy, she is given a course of a bispecific antibody fusion protein consisting of a recombinant heteroconjugate of an anti-CD74 and an anti-histone (IMMU-H4) antibody, at a dose of 500 mg i.v. weekly times 4 weeks. At evaluation at 2 months later, she has a marked improvement in all organ systems, to a BILAG C and D status in most, and is capable of having her prednisone dose tapered to 6.5 mg per day. At follow-up of 3 months, most of her organ symptoms remain stable, and she remains on this low does of prednisone without any flare.

Example 10. Therapy of Non-Hodgkin's Lymphoma (NHL)

T M is a 68-year-old white male with a history of diffuse large B-cell NHL that has relapsed after therapy with standard cycles of CHOP chemotherapy and rituximab, and is now presenting with fever, lung and mediastinal infiltrates, enlarged cervical and axillary lymph nodes, spleen, and evidence of bone marrow involvement based on aspiration and cytology. He receives 6 weekly infusions of two humanized antibodies, one against histone (IMMU-H4) and the other against CD20 (veltuzumab), each given on the same day sequentially, over a 3-4-hr infusion for each, at a dose of each of 200 mg. Four days after the last infusion, his examination indicates no major toxicities to the therapy, and some palpable softening of his cervical and axillary lymph nodes, and a reduction in the size of his spleen by palpation. At the next follow-up examination in 8 weeks, almost all of his cervical and about half of these axillary nodes have disappeared, including normalization of the spleen size, and his chest x-ray and CT scan show evidence of about a 50% shrinkage of his pulmonary and mediastinal infiltrates. About 4 months later, his examination reveals that although his lymph node and pulmonary involvement are stable, there is a suggested increase in bone marrow involvement and a drop in his Hg to 7 g/dL and a platelet fall to 55,000/μL. He then receives a bispecific antibody consisting of a fused humanized antibody against MIF and humanized antibody against histone (IMMU-H4 antibody), given twice weekly for 3 weeks at a dose of 200 mg per slow i.v. infusion. At his 3-month evaluation, his Hg shows a rise to 11 g/dL and his platelets rise to 120,000/μL, there is a remarkable decrease of NHL cells in the bone marrow aspirate, and there are no lymph nodes palpable or disease visible in the chest by radiological examinations. The patient's response remains stable for another 4 months.

Example 11. Therapy of Cancer-Related Cachexia

J. M. is a 68-year-old Caucasian male with a history of heavy cigarette smoking and an inoperable small-cell lung cancer affecting his right lung and paraortic and parabronchial lymph nodes on both sides. He has received combination chemotherapy, which has shown myelotoxicities and evidence of some minor tumor shrinkage, being less than 30% of all measurable volume. He presents with considerable weight loss, being almost 2 meters high and now weighing 58 kg, suffering from cancer-related cachexia. He is infused weekly for 8 weeks with a humanized bispecific fusion antibody construct targeting both IL-6 and histone (IMMU-H4 antibody), at a dose of 120 mg weekly. During the last 2 weeks, his appetite improves, and he shows a weight gain to 65 kg at 7 weeks post therapy, with more muscle strength and generally improved vigor, which then remains stable at 70-75 kg over the next 2 months, when he begins to show progression of his malignant disease. Other than his cyclic chemotherapy, no corticosteroids were given during the antibody therapy, and he is considered to have responded to this treatment for cachexia.

Example 12. Therapy of Immune Thrombocytopenia (ITP)

S. R. is a 32-year-old female who has a history of spontaneous for 2 years and has been responsive to corticosteroid therapy with prednisone given at high doses for several courses. She now presents with severe ITP, bruising and petecchiae, and a platelet count of 12,000/μL. She also complains of frequent gum and nose bleeding. She is given four doses of dexamethasone (40 mg) over two weeks, combined with a humanized bispecific antibody construct made by DNL® from humanized anti-CD20 (veltuzumab) and humanized anti-histone (IMMU-H4) antibodies at a weekly subcutaneous dose of 200 mg for three weeks. Blood count examination 2 weeks later indicates a reduction of B cells by 80% and an increase in platelets to 38,000/μL, with reduced bruising, petecchiae, and bleeding manifestations. Two weeks later, her platelets rise further to 55,000/uL. She returns 2 months later for a repeated cycle of this therapy, and then shows a rise of her platelets to 100,000/μL, considered as a complete response. This level is maintained for 3 months, when tested last.

What is claimed is:

1. A chimeric or humanized anti-histone H3 antibody or antigen-binding fragment thereof, comprising the heavy chain CDR sequences CDR1 (SYWMH, SEQ ID NO:100), CDR2 (NIDPSDSETHYNQKFKD, SEQ ID NO:101) and CDR3 (EKITDDYNYFDY, SEQ ID NO:102) and the light chain CDR sequences CDR1 (RASESVDSYGNSFMH, SEQ ID NO:103), CDR2 (HASNLES, SEQ ID NO:104) and CDR3 (QQNNEDPLT, SEQ ID NO:105), wherein the antibody or antigen-binding antibody fragment is conjugated to at least one therapeutic or diagnostic agent.

2. The chimeric or humanized antibody or fragment thereof of claim 1, wherein the therapeutic agent is selected from the group consisting of a second antibody, a second antibody fragment, a radionuclide, an immunomodulator, an anti-angiogenic agent, a pro-apoptotic agent, a cytokine, a chemokine, a drug, a toxin, a hormone, an siRNA and an enzyme.

3. The chimeric or humanized antibody or fragment thereof of claim 2, wherein the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, temazolomide (an aqueous form of DTIC), transplatinum, thalidomide, thioguanine, thiotepa, teniposide, topotecan, uracil mustard, vinorelbine, vinblastine, vincristine, a vinca alkaloid, a tyrophostin, canertinib, dasatinib, erlotinib, gefitinib, imatinib, lapatinib, leflunomide, nilotinib, pazopanib, semaxinib, sorafenib, sunitinib, sutent, vatalanib, PCI-32765 (ibrutinib), PCI-45292, GDC-0834, LFM-A13 and RN486.

4. The chimeric or humanized antibody or fragment thereof of claim 2, wherein the toxin is selected from the group consisting of ricin, abrin, alpha toxin, saporin, ribonuclease (RNase), ranpirnase, DNase I, Staphylococcal enterotoxin-A, pokeweed antiviral protein, gelonin, diphtheria toxin, Pseudomonas exotoxin, and Pseudomonas endotoxin.

5. The chimeric or humanized antibody or fragment thereof of claim 2, wherein the immunomodulator is selected from the group consisting of a cytokine, a stem cell growth factor, a lymphotoxin, a hematopoietic factor, a colony stimulating factor (CSF), an interleukin (IL), erythropoietin, thrombopoietin, tumor necrosis factor (TNF), granulocyte-colony stimulating factor (G-CSF), granulocyte macrophage-colony stimulating factor (GM-CSF), interferon-α, interferon-β, interferon-γ, interferon-λ, TGF-α, TGF-β, interleukin-1 (IL-1), IL-1a, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, FLT-3, angiostatin, thrombospondin, endostatin and lymphotoxin.

6. The chimeric or humanized antibody or fragment thereof of claim 5, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factors, interferon-α, interferon-β, interferon-γ, macrophage-CSF (M-CSF), IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

7. The chimeric or humanized antibody or fragment thereof of claim 2, wherein the radionuclide is selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Rh, $^{149}$Pm, $^{169}$Er, $^{194}$Ir, $^{58}$Co, $^{80m}$Br, $^{99m}$Tc, $^{103m}$Rh, $^{109}$Pt, $^{119}$Sb, $^{125}$, $^{189m}$Os, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{125m}$Te, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br, $^{169}$Yb and $^{227}$Th.

8. The chimeric or humanized antibody fragment of claim 1, wherein the antibody fragment is selected from the group consisting of F(ab')2, Fab', Fab, Fv and scFv.

9. The chimeric or humanized antibody or fragment thereof of claim 1, wherein the diagnostic agent is selected from the group consisting of a radionuclide, a radiological contrast agent, a paramagnetic ion, a metal, a fluorescent label, a chemiluminescent label, an ultrasound contrast agent and a photoactive agent.

10. The chimeric or humanized antibody or fragment thereof of claim 9, wherein the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb and $^{83}$Sr.

11. The chimeric or humanized antibody or fragment thereof of claim 9, wherein the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

12. The chimeric or humanized antibody or fragment thereof of claim 9, wherein the fluorescent label is selected from the group consisting of Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4', 5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red.

13. A fusion protein comprising a chimeric or humanized antibody or fragment thereof of claim 1.

14. A therapeutic composition comprising a chimeric or humanized antibody or fragment thereof of claim 1.

15. A chimeric or humanized anti-histone H2B antibody or antigen-binding fragment thereof, comprising the heavy chain CDR sequences CDR1 (SYVMY, SEQ ID NO:110), CDR2 (YINPYNDGTKYNEKFKG, SEQ ID NO:111) and CDR3 (PGDGYPFDY, SEQ ID NO:112) and the light chain CDR sequences CDR1 (RSSQSIVHSNGNTYLE, SEQ ID NO:113), CDR2 (KVSNRFS, SEQ ID NO:114) and CDR3 (FQGSHVPYT, SEQ ID NO:115), wherein the antibody or antigen-binding antibody fragment is conjugated to at least one therapeutic or diagnostic agent.

16. The chimeric or humanized antibody or fragment thereof of claim 15, wherein the therapeutic agent is selected from the group consisting of a second antibody, a second antibody fragment, a radionuclide, an immunomodulator, an anti-angiogenic agent, a pro-apoptotic agent, a cytokine, a chemokine, a drug, a toxin, a hormone, an siRNA and an enzyme.

17. The chimeric or humanized antibody or fragment thereof of claim 16, wherein the drug is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosourea, plicomycin, procarbazine, paclitaxel, pentostatin, PSI-341, raloxifene, semustine, streptozocin, tamoxifen, temazolomide (an aqueous form of DTIC), transplatinum, thalidomide, thioguanine, thiotepa, teniposide, topotecan, uracil mustard, vinorelbine, vinblastine, vincristine, a vinca alkaloid, a tyrophostin, canertinib, dasatinib, erlotinib, gefitinib, imatinib, lapatinib, leflunomide, nilotinib, pazopanib, semaxinib, sorafenib, sunitinib, sutent, vatalanib, PCI-32765 (ibrutinib), PCI-45292, GDC-0834, LFM-A13 and RN486.

18. The chimeric or humanized antibody or fragment thereof of claim 16, wherein the toxin is selected from the group consisting of ricin, abrin, alpha toxin, saporin, ribonuclease (RNase), ranpirnase, DNase I, Staphylococcal enterotoxin-A, pokeweed antiviral protein, gelonin, diphtheria toxin, *Pseudomonas* exotoxin, and *Pseudomonas* endotoxin.

19. The chimeric or humanized antibody or fragment thereof of claim 16, wherein the immunomodulator is selected from the group consisting of a cytokine, a stem cell growth factor, a lymphotoxin, a hematopoietic factor, a colony stimulating factor (CSF), an interleukin (IL), erythropoietin, thrombopoietin, tumor necrosis factor (TNF), granulocyte-colony stimulating factor (G-CSF), granulocyte macrophage-colony stimulating factor (GM-CSF), interferon-α, interferon-β, interferon-γ, interferon-λ, TGF-α, TGF-β, interleukin-1 (IL-1), IL-1a, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-23, IL-25, LIF, FLT-3, angiostatin, thrombospondin, endostatin and lymphotoxin.

20. The chimeric or humanized antibody or fragment thereof of claim 19, wherein the cytokine is selected from the group consisting of human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, tumor necrosis factor-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), osteoinductive factors, interferon-α, interferon-β, interferon-γ, macrophage-CSF (M-CSF), IL-1, IL-1a, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, tumor necrosis factor and lymphotoxin.

21. The chimeric or humanized antibody or fragment thereof of claim 16, wherein the radionuclide is selected from the group consisting of $^{111}$In, $^{111}$At, $^{177}$Lu, $^{211}$Bi, $^{212}$Bi, $^{213}$Bi, $^{211}$At, $^{62}$Cu, $^{67}$Cu, $^{90}$Y, $^{125}$I, $^{131}$I, $^{133}$I, $^{32}$P, $^{33}$P, $^{47}$Sc, $^{111}$Ag, $^{67}$Ga, $^{153}$Sm, $^{161}$Tb, $^{152}$Dy, $^{166}$Dy, $^{161}$Ho, $^{166}$Ho, $^{186}$Re, $^{188}$Re, $^{189}$Re, $^{211}$Pb, $^{212}$Pb, $^{223}$Ra, $^{225}$Ac, $^{77}$As, $^{89}$Sr, $^{99}$Mo, $^{105}$Rh, $^{149}$Pm, $^{169}$Er, $^{194}$Ir, $^{58}$Co, $^{80m}$Br, $^{99m}$Tc, $^{103m}$Rh, $^{109}$Pt, $^{119}$Sb, $^{125}$I, $^{189m}$Os, $^{192}$Ir, $^{219}$Rn, $^{215}$Po, $^{221}$Fr, $^{255}$Fm, $^{11}$C, $^{13}$N, $^{15}$O, $^{75}$Br, $^{198}$Au, $^{199}$Au, $^{224}$Ac, $^{77}$Br, $^{113m}$In, $^{95}$Ru, $^{97}$Ru, $^{13}$Ru, $^{105}$Ru, $^{107}$Hg, $^{203}$Hg, $^{121m}$Te, $^{125m}$Te, $^{165}$Tm, $^{167}$Tm, $^{168}$Tm, $^{197}$Pt, $^{109}$Pd, $^{142}$Pr, $^{143}$Pr, $^{161}$Tb, $^{57}$Co, $^{58}$Co, $^{51}$Cr, $^{59}$Fe, $^{75}$Se, $^{201}$Tl, $^{76}$Br, $^{169}$Yb and $^{227}$Th.

22. The chimeric or humanized antibody fragment of claim 15, wherein the antibody fragment is selected from the group consisting of F(ab')$_2$, Fab', Fab, Fv and scFv.

23. The chimeric or humanized antibody or fragment thereof of claim 15, wherein the diagnostic agent is selected from the group consisting of a radionuclide, a radiological contrast agent, a paramagnetic ion, a metal, a fluorescent label, a chemiluminescent label, an ultrasound contrast agent and a photoactive agent.

24. The chimeric or humanized antibody or fragment thereof of claim 23, wherein the radionuclide is selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb and $^{83}$Sr.

25. The chimeric or humanized antibody or fragment thereof of claim 23, wherein the paramagnetic ion is selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

26. The chimeric or humanized antibody or fragment thereof of claim 23, wherein the fluorescent label is selected from the group consisting of Alexa 350, Alexa 430, AMCA, aminoacridine, BODIPY 630/650, BODIPY 650/665, BODIPY-FL, BODIPY-R6G, BODIPY-TMR, BODIPY-TRX, 5-carboxy-4', 5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, Fluorescein, HEX, 6-JOE, NBD (7-nitrobenz-2-oxa-1,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, ROX, TAMRA, TET, TRIT (tetramethyl rhodamine isothiol), Tetramethylrhodamine, and Texas Red.

27. A fusion protein comprising a chimeric or humanized antibody or fragment thereof of claim 15.

28. A therapeutic composition comprising a chimeric or humanized antibody or fragment thereof of claim 15.

* * * * *